(12) United States Patent
Van Rijn et al.

(10) Patent No.: US 7,531,120 B2
(45) Date of Patent: May 12, 2009

(54) METHOD OF MAKING A PRODUCT WITH A MICRO OR NANO SIZED STRUCTURE AND PRODUCT

(75) Inventors: Cornelis Johannes Maria Van Rijn, Hengelo (NL); Laura Vogelaar, Enschede (NL); Wietze Nijdam, Enschede (NL); Jonathan Nathaniel Barsema, Enschede (NL); Matthias Wessling, Enschede (NL)

(73) Assignee: Aquamarijn Holding B.V., Hengelo (NL)

( * ) Notice: Subject to any disclaimer, the term of this patent is extended or adjusted under 35 U.S.C. 154(b) by 0 days.

(21) Appl. No.: 10/433,275

(22) PCT Filed: Dec. 3, 2001

(86) PCT No.: PCT/NL01/00874

§ 371 (c)(1),
(2), (4) Date: Sep. 29, 2003

(87) PCT Pub. No.: WO02/43937

PCT Pub. Date: Jun. 6, 2002

(65) Prior Publication Data

US 2004/0028875 A1    Feb. 12, 2004

(30) Foreign Application Priority Data

Dec. 2, 2000   (NL) .................................... 1016779

(51) Int. Cl.
*B29C 39/00* (2006.01)
(52) U.S. Cl. ....................................... 264/299; 264/319
(58) Field of Classification Search ................. None
See application file for complete search history.

(56) References Cited

U.S. PATENT DOCUMENTS

| | | | |
|---|---|---|---|
| 3,357,052 A | | 12/1967 | Vos |
| 4,770,777 A | | 9/1988 | Steadly et al. |
| 4,872,888 A | | 10/1989 | Hagmann et al. |
| 5,256,360 A | | 10/1993 | Li |
| 5,281,511 A | | 1/1994 | Gerhardt |
| 5,620,790 A | | 4/1997 | Holzki et al. |
| 5,660,680 A | | 8/1997 | Keller |
| 5,868,976 A | | 2/1999 | Puglia et al. |
| 6,071,406 A | * | 6/2000 | Tsou ..................... 210/500.41 |
| 6,132,858 A | * | 10/2000 | Kloos ...................... 428/32.32 |
| 6,423,252 B1 | * | 7/2002 | Chun et al. ................... 264/28 |

FOREIGN PATENT DOCUMENTS

| | | |
|---|---|---|
| DE | 35 18 569 | 11/1986 |
| EP | 0 362 588 | 4/1990 |

(Continued)

OTHER PUBLICATIONS

Patent Abstracts of Japan, vol. 1996, No. 2, Feb. 29, 1996.

*Primary Examiner*—Monica A Huson
(74) *Attorney, Agent, or Firm*—Young & Thompson

(57) ABSTRACT

Using phase separation technique perforated as well as non-perforated polymeric structures can be made with high aspect ratios (>5). By varying the phase separation process the properties (e.g. porous, non-porous, dense, open skin) of the moulded product can be tuned. Applications are described in the field of micro fluidics (e.g. micro arrays, electrophoretic boards), optics, polymeric solar cells, ball grid arrays, and tissue engineering.

10 Claims, 16 Drawing Sheets

FOREIGN PATENT DOCUMENTS

| | | |
|---|---|---|
| EP | 0 382 420 | 8/1990 |
| EP | 0 594 007 | 4/1994 |
| EP | 1 002 830 | 5/2000 |
| GB | 1 584 589 | 2/1981 |
| WO | WO 95/30793 | 11/1995 |
| WO | WO 99/04891 | 2/1999 |
| WO | WO 99/64580 | 12/1999 |

* cited by examiner

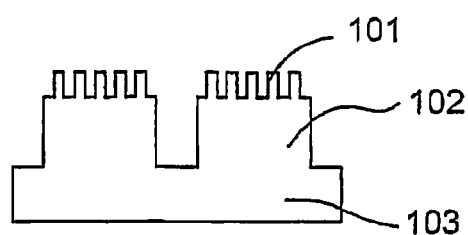
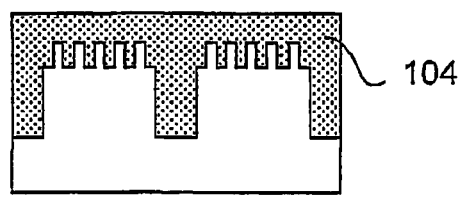
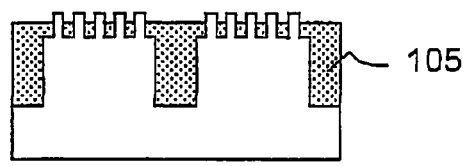
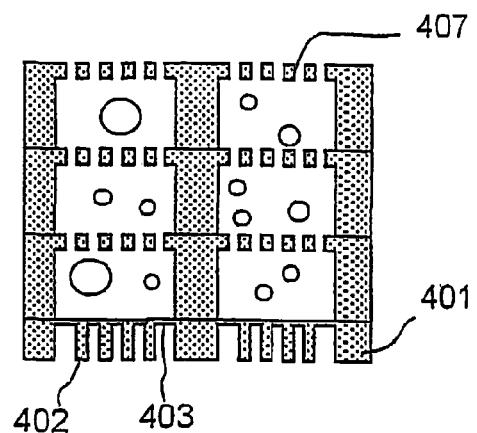
Fig. 4
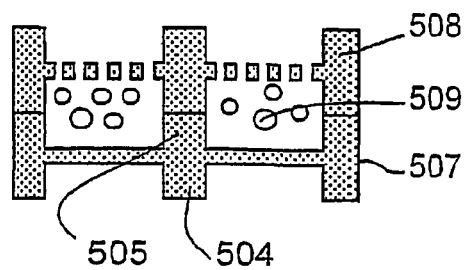
Fig. 5
Fig. 1

METHOD OF MAKING A PRODUCT WITH A MICRO OR NANO SIZED STRUCTURE AND PRODUCT

The invention relates to a method of making a product with a micro to nano sized structure using a mould having a corresponding structure at a mould surface in which a fluid containing a casting material is brought into contact with said mould surface.

The moulding of products with micro-structures featuring high aspect ratio's in the micron and sub-micron range is relatively difficult because of the mechanical fragility, distortion and anchoring of those structures during release of the products from the corresponding mould. Injection moulding, pressure moulding, hot embossing, slip casting, cross linking of the product on the mould are known techniques. The moulds or stamps themselves, with the desired micro pattern of grooves, ridges and wells, are relatively straightforward to fabricate using well known laser drilling, spark erosion, photo lithographic and anisotropic etching techniques. The fabrication of these moulds however turns out to be rather expensive and can therefore not be applied for economical production of the intended products. Moreover, a successful, reproducible release from the mould of the products concerned, with their delicate microstructure, remains complicated.

To facilitate said release and to avoid distortion of the high aspect ratio micro-structures a method of the above kind has been disclosed in U.S. Pat. No. 5,660,680 (Keller) in which sacrificial layers are applied between the mould and the product in subsequent process steps. The removal and re-deposition of such sacrificial layers is however complicated and time consuming, which renders the process less suitable for application on an industrial scale.

Accordingly, there remains a need for economical moulding of micro-structured products that can be made out of a wide variety of polymeric and inorganic materials. The present invention, hence, has for its object inter alia to provide a method of producing articles having nano and micro-structured surfaces made from a broad variety of materials which can be applied in a economical and reproducible manner allowing for an industrial scale.

In order to attain said object a method according to the invention is characterized in that the fluid is subjected to a treatment to induce phase separation therein, in that the said casting material is at least partially solidified on the mould surface and in that the resulting product is released from the mould surface. It has surprisingly been found that due to said phase-separation a relatively dense and highly flat skin layer is formed at the interface with said mould surface which is conformal to said surface. The resulting product moreover tends to shrink isotropically to a certain extent due to the phase separation process. These two circumstances greatly improve the release of the eventual product from the mould without notable distortion of the microstructure.

Phase separation entails the process of changing a one-phase casting fluid (solution) into at least two separate phases. One phase is defiled to be uniform in chemical composition and in physical structure throughout the material. In all phase separation processes, a casting solution is precipitated into at least two phases: a solid material-rich phase that forms the matrix of the product and a material-poor phase that may form the inner product pores. The phase separation is generally a thermodynamically driven process and may be induced on the mould (or shortly prior or after casting) by changing e.g. the composition of the solution, the temperature or the pressure of the casting solution. The composition of the casting solution may be changed by bringing the casting solution in contact with a non-solvent, which is normally a gas (vapour) or a liquid not well miscible with the material, or by evaporating a solvent from a casting solution containing a non-solvent, or by reaction of components in the casting solution resulting in a non-solvent agent. The material of the product may be (mainly) polymeric as well as inorganic. According to the invention the casting solution does not have to be vulcanised or cross linked on the mould to induce solidification as is commonly used for injection or other (one phase) cast moulding techniques. The solidification technique according to the invention is a relatively fist process in comparison with other known techniques. One may of coarse also cross link or cure during or preferably after release from the mould to improve functional properties of the phase separated product.

Another advantage of the use of phase separation techniques is that dense products as well as micro and nano porous products with a closed cell structure (non-connected cells) as well as an open cell structure (connected cells) can be obtained. The cell structure may be anisotropic in porosity as well as in pore size throughout its thickness. Porous structures have improved elastic properties facilitating the release of high aspect ratio structures from the mould in comparison with dense structures of the same material. Also the formation and progress of cracks in the moulded material is inhibited and stopped by the presence of micro pores in the material. Whereas normally aspect ratio's (height/wide) of 1-2 are achieved in dense materials, according to the invention aspect ratio's larger than 2-5, and preferably larger than 5-10 are achieved in microporous products made from the same material. Microporous materials can also easily be redissolved in short time depending on the application (e.g. sacrificial moulding). The porous material can further be functionalised with many different physical/chemical/biological reaction techniques. Also functional fluid transport through the micro pores creates new applications as micro contact printing.

Ceramic micro-structured products are of coarse more sensitive for distortion (cracking) than polymeric materials. With polydimethylsiloxane relatively high aspect ratio structures could be formed in a reproducible manner owing to its superior elastic properties. Other polymeric materials suitable for relatively low aspect ratio microstructures include, polymethylmethacrylate, polyurethane, polyvinylchloride, polystyrene and polycarbonate. On the other hand suitable polymeric and inorganic materials should be based upon their compatibility with the conditions present in the particular operation to be performed by the product, e.g. demands on pH, temperature, biocompatibility, electric/thermal conductivity, optical and wetting properties. An extension of the applicable materials would of course be welcomed to meet all required demands.

In a further aspect, the invention features a novel process for preparing a product that includes bringing a mouldable material and the surface of an open mould into contact with each other to imprint a micro architecture onto the mouldable material. The resulting product is then separated from the moulding surface of the tool. An "open mould" is a moulding tool that has an exposed moulding surface. It is an important recognition of the invention that hitherto no use has been made of phase separation techniques in combination with an open mould to obtain products with a micro to nano-structured surface. The advantage of an open moulding tool is that the products can be made in the form of an inexpensive and fast roll good by bringing the mouldable material and mould in a constant relative movement (e.g. continuous sheet imprinting or 3D extrusion with a micro-structured spinneret).

Preferably the phase separation and solidification of the product is mainly induced during moulding because the induced shrinkage of the casting solution can be tuned (depending on the exact phase separation conditions) in order to prevent anchoring and distortion of the product during release from the mould. The phase separation may also be completed after removal of the product from the mould, this is advantageous in case time consuming steps are needed.

The process of phase separation can be proceeded at relatively low working temperatures which normally leads to a controllable shrinkage of the initial casting material to a microporous product without the formation of cracks as is often observed in (nonporous) solid hot embossed or injection moulded structures with a high aspect ratio. Surprisingly it has been found that even fully perforated micro-structures (perforation diameter <5 micron) can be made in thin sheet products (thickness <30 micron) without release difficulties, an advantage that out-beats all present micro-moulding techniques.

The types of phase separation processes are classified into six categories:

1) vapour-induced phase separation (VIP), also called "dry casting" or "air casting". Evaporation of the liquid (solvent) will result in a dense or porous product depending on the material and the used solvent/solute mixtures; The vapour may contain water or organic solvent molecules that may be absorbed by the casted film and will influence the porosity of the product.

2) liquid-induced phase separation (LIPS), mostly referred to as "immersion casting" or "wet casting". This process normally yields dense or porous products depending on the material and the used solvents and non-solvent mixtures. This technique may be combined with 1) for polymer solutions with e.g. two solvents with different boiling points.

3) Thermally induced phase separation (TIPS), frequently called "melt casting"; The material may solidify to a dense or porous product of a material-solvent-additive mixture by varying the temperature of the material-solvent during the casting process.

4) Colloidal induced phase separation (CIPS). A phase separated colloidal solution is used to perform structure arrestment on the micro fabricated mould. For example, a polymerizable bicontinuous microemulsion can be applied onto the mould, or a sol/gel mixture of a ceramic material. The pore morphology can be tuned by the addition of a co-solvent resulting generally into smaller pores.

5) Pressure induced phase separation (PIPS), "pressure casting"; The casting solution may contain for example a saturated dissolved gas. Reduction of the pressure (or increase of temperature) will induce growth of gas cells in the casting solution with a closed cell or open cell morphologies and a typical size of 0.01-1000 micron.

6) Reaction-induced phase separation (RIPS), a casting solution containing monomers start to react and initiate phase separation due to for instance increase in molecular weight or production of a non-solvent Most common phase separation processes are based on phase separation of a polymer solution. by bringing the casting solution into contact with a non-solvent, which is normally a gas (vapour) or a liquid not well miscible with the solvent of the casting solution.

When a system is chosen with a solvent and a non-solvent having a strong interaction, immersing the polymer solution in such a non-solvent results in instantaneous demixing. This process is characterised by the formation of a thin and relatively dense skin layer and in inner percolating open cell morphologies of the product. Examples of such systems are N-methyl pyrrolidone(NMP), dimethylsulfoxyde (DMSO), dimethylfluoride (DMF) or dimethylacetamide (DMAc) as solvent and water as non-solvent. When the system is chosen with a poor interaction between solvent and non-solvent, immersing the polymer solution in such a non-solvent results in delayed demixing. This process is characterised by extremely thick and dense skin layers. To some extend, the cell walls show ruptures connecting one or more cells with each other, however, overall the morphology is non-percolating disabling any significant liquid transport wicking the inner porous part of the product.

Examples of such systems are: acetone and THF as solvent and water as non-solvent or NMP, DMAc, DMF, DMSO as solvent and higher alcohols (like butanol, pentanol, octanol) or glycols as non-solvent. A third system that can be distinguished is the immersion of a polymer solution in a mixture of solvent and non-solvent. This process also results in delayed demixing, but gives normally very porous skin layers. The first delayed demixing process is characterised by upon immersion and prior to phase separation; the polymer solution densities. The second process is characterised by dilution of the polymer solution upon immersion and prior to phase separation.

Further, more complicated formulations can be handled when using this type of process. The number of polymeric materials that can be used for phase separation techniques outnumber the present available polymeric materials used for hot embossing. Chemical inert materials such as polyimide, perfluoronated polymers such as Teflon® and Hyflon®, polyethersulfone and many other new materials can now be used for the preparation of products in the form of a roil good. The porous morphology of the product can be influenced by the addition of low molecular weight additiv s such as ethylen glycol, aliphatic alcohols and surfactants. Optical transparent products may be obtained through the use of nano porous (poresize <50 nm) phase separation techniques. Fluor-taylored polymers of e.g. polycarbonate, polymethyl methacrylate, polyarylates and polyimides may be used for a reduced optical absorption in optical wave-guide applications.

Phase separation of a polymer solution can also be performed when the solution contains inorganic filler materials such as small silica, siliconnitride, titaniumdioxyde, alumina or zirconia, beriliumoxyde, siliconcarbide. The inorganic filler may be added to influence the porosity or to prepare a polymer/inorganic precursor. Such a precursor may be fired in vacuum or in an inert or slightly oxidative environment to high temperature resulting in polymer degradation and simultaneous agglomeration of inorganic particles and fusion into a fully ceramic microtextured ceramic for e.g. titaniumdioxyde based solar cells.

If the porous morphologies show a percolating porosity, one may fill the pores by various methods to either close the pores to prevent any liquid penetration or to functionalize the porous system. Impregnation with a reactive monomer such as methyl methacrylate and subsequent polymerisation may act as choice for pore closure. Photochemical grafting of reactive monomers such 4-vinylpyridine allows the filling of pores with a hydrophilic network inside the stiff support matrix. Filling the pores with a monomer such as pyrrole allows the polymerisation into polypyrrole such that the polypyrrole can act as an electron conducting polymer stabilised by porous support matrix.

The porous polymer developing during phase separation can also be functionalized by metal particles. The metal is generally incorporated by the following method: impregnation of the porous support with a metal ion solution and subsequent reduction. Here, the expert in the field can draw from various preparation routes in catalyst development. One may think of precipitation of silver nitrate into the pores and subsequent heat treatment at elevated temperatures. Reduction of a impregnated metal ion solution of a palladium acetate in methyletherketone (MEK) by $NaBH_4$ solution in a mixture of methanol and water for instance also causes the metal to reduce into to small metallic clusters.

Hydrophilisation of micro-structured architectures with outer surfaces and inner surfaces inside the porous morphology can be carried out by various methods. A coating of polyvinyl pyrrolidone applied by dip-coating or spin-coating from a solution with water or any other solvent alters the surface hydrophilic. If intimate adhesion between the micro-textured material and the PVP is required, one preferably wants to perform the coating from a solution comprising a common solvent for both polymers. The PVP may be crosslinked by a persulfate after-treatment or heat treatment so that it does not re-dissolve after contact with any solvent during application.

Hydrophilisation as well as hydrophobisation can further be achieved by applying a subsequent plasma treatment using carbon dioxide, oxygen or ammonia as a reacting gas. Gases containing fluorine, such as CF4, result in hydrophobic and super-hydrophobic surfaces.

Besides rendering the outer or inner surface hydrophilic or hydrophobic, one may wish to activate the surface wet chemically. To the expert familiar with the synthesis of chromatographic materials, such activation techniques are apparent. Enzymes, proteins, nucleic acids, amino acids, oligonucleotides, antibodies, or antigens may than be bound to the activated surface to serve as bio-catalytic product or as an affinity adsorption product.

Typically, the products of the present invention are fabricated in two or more parts.

Specifically, a first planar product element is provided having a plurality of grooves and/or wells, corresponding to the fluid channels and/or chambers, manufactured, e.g., moulded or machined, into one of its planar surfaces. These grooves provide the bottom and side walls of the channels and chambers of the devices. A second planar product element is then mated with the first to define the top wall of the channels and chambers. The two members are bonded together in order to ensure that the chann1s and chambers in the product are fluid tight.

Bonding of the two members may be accomplished by a number of methods that are known in the art, such as through the use of adhesives, e.g., UV curable adhesives, or by sonically welding one member to the other.

It is a further object of the present invention to provide a moulding method which replicates micron and sub-micron features (<500 micron) with high resolution and high aspect ratio's between 2-5 and preferably larger than 5.

The manufacturing process offers significant design flexibility, enabling a number of processing steps to be performed in-line. For example, microelectronic, microoptical, and/or micromechanical elements can be readily incorporated into the article during manufacture in a variety of different ways, including as part of the product bearing e.g. the microfluid processing architecture, as part of a cover layer, or as part of a second polymeric product integrally bonded to the product. Various designs incorporating these microelements are also possible.

The invention further relates to a product having a porous base structure which is at least partly covered by a more dense skin layer as well as to a product moulded in a product according to the invention, as will al more readily be understood based on the following specific embodiments, examples and accompanying drawings.

DETAILED DESCRIPTION OF THE INVENTION WITH SPECIFIC EMBODIMENTS

FIG. 1 shows process steps for the manufacturing of a microsieve,

Figure 9A:
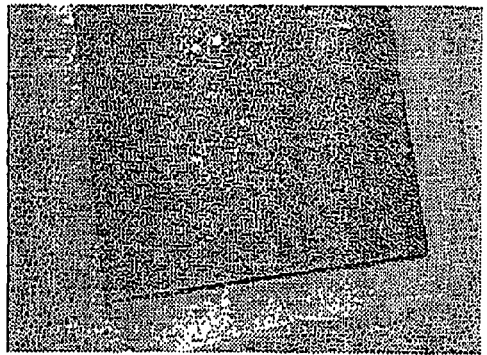
Figure 9B:
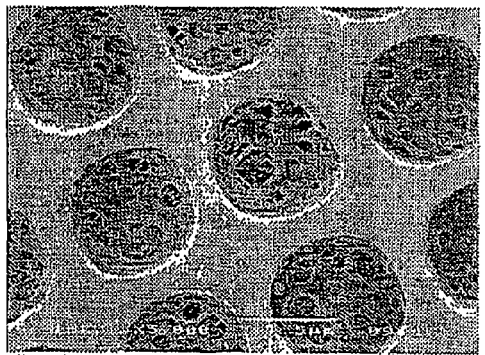
Figure 7:
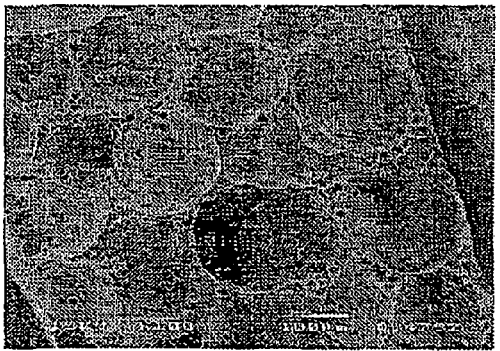
Figure 6:
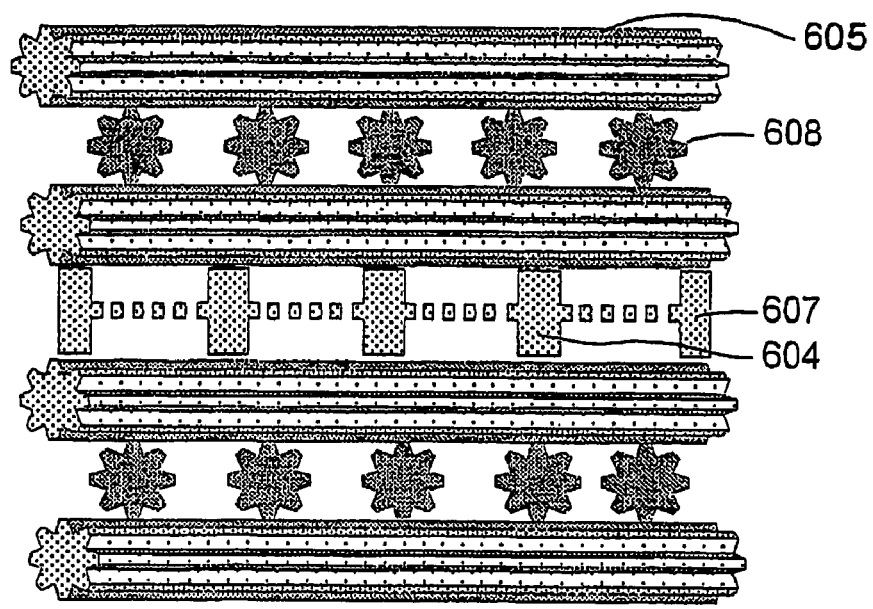
Figure 8:
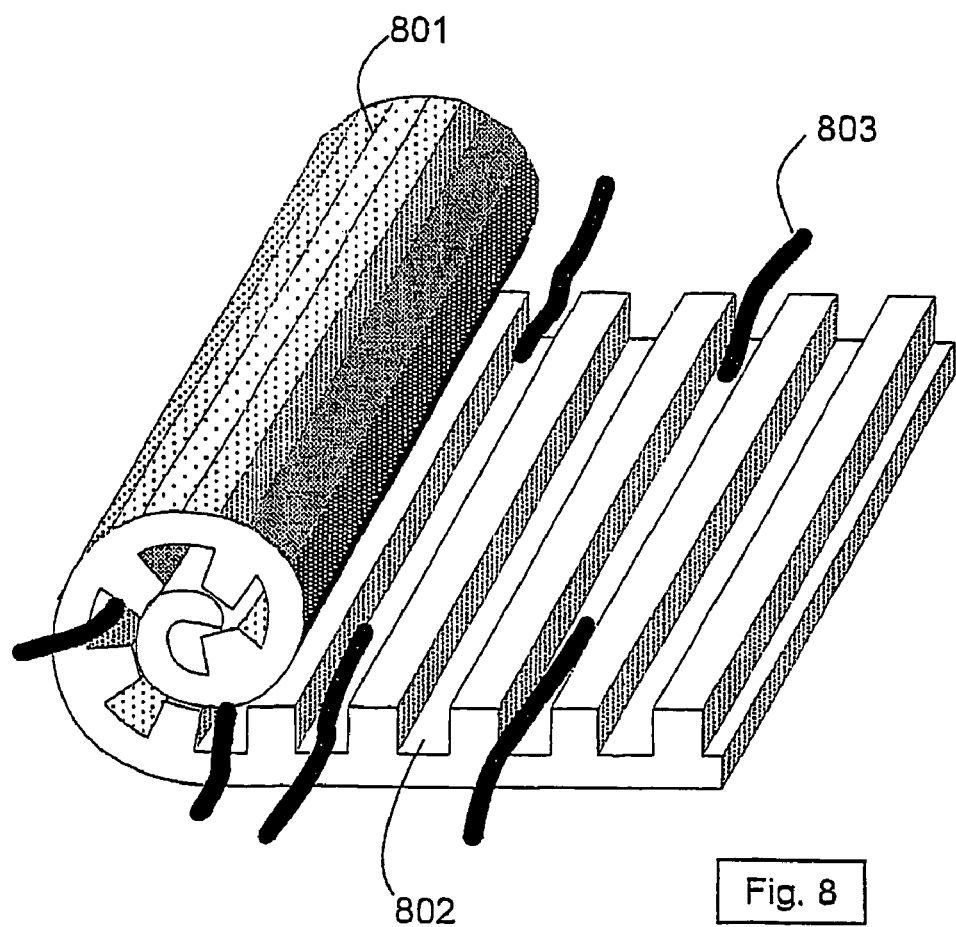
Figure 10:
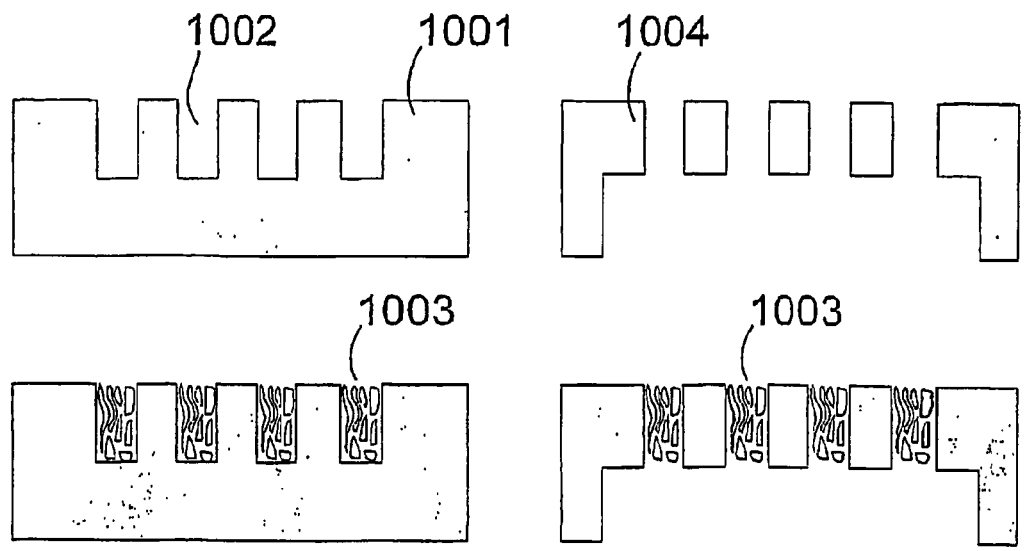

FIG. 4 shows a stack of a filtration membrane and microsieves for encapsulation of cells, FIG. 5 shows a similar stack with a support on both sides of the membrane, FIG. 6 shows a biodegradable 3D scaffold structure with a microsieve and extruded fibre with a microstructure, FIG. 7 shows a SEM picture of a fibre with a bimodal pore size distribution, FIG. 8 shows a folded tube with a microstructure to enable nerve cell growth, FIGS. 9A,9B show SEM pictures of multiwell/microtitration plate structures, FIG. 10 shows different embodiments of a hybrid microarray structure.

Figure 12A:
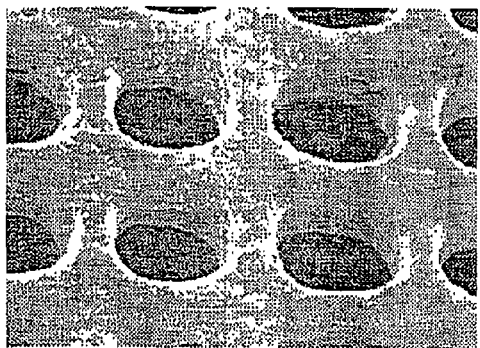
Figure 11:
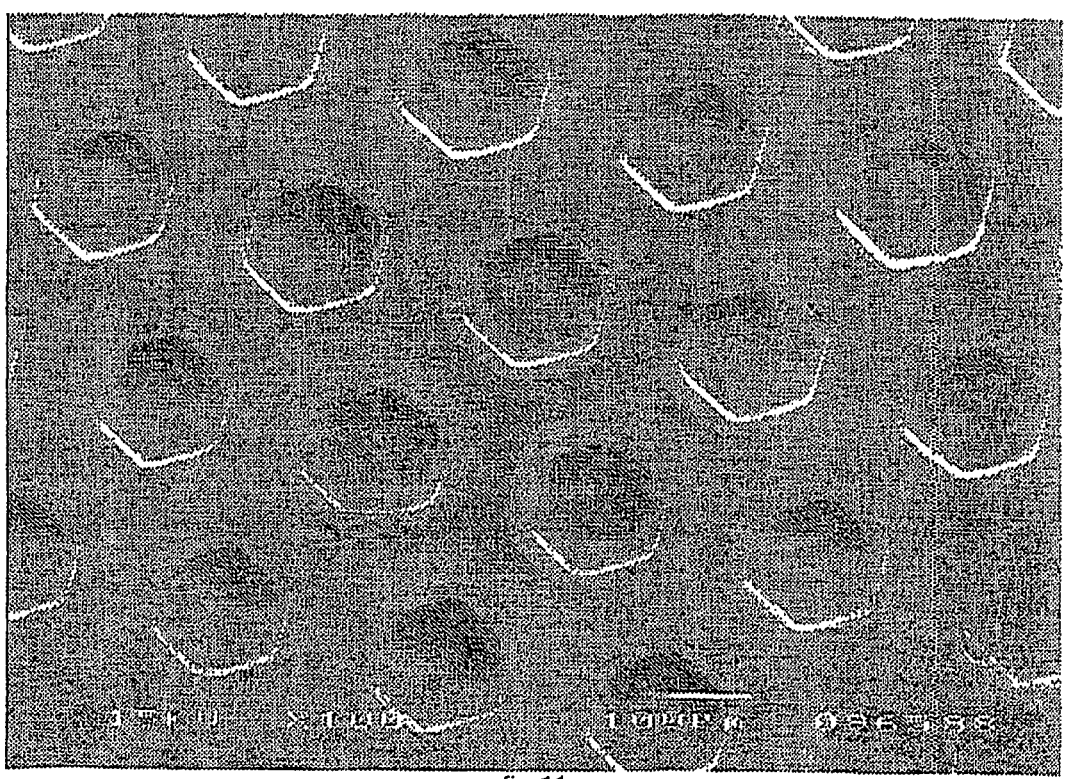
Figure 12B:
Figure 15A:
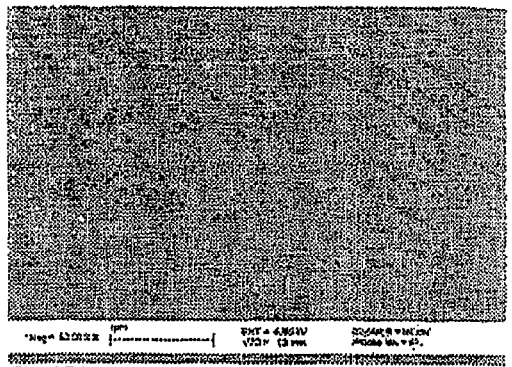
Figure 14:
Figure 21B:
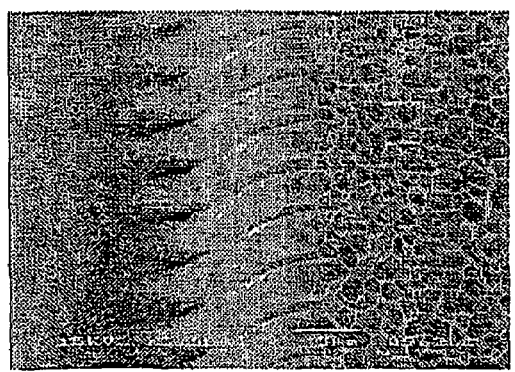
Figure 23:
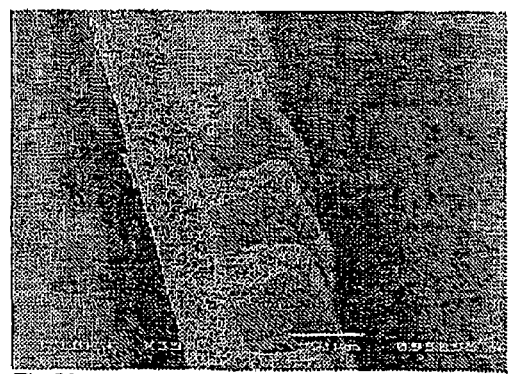
Figures 13A, 13B:
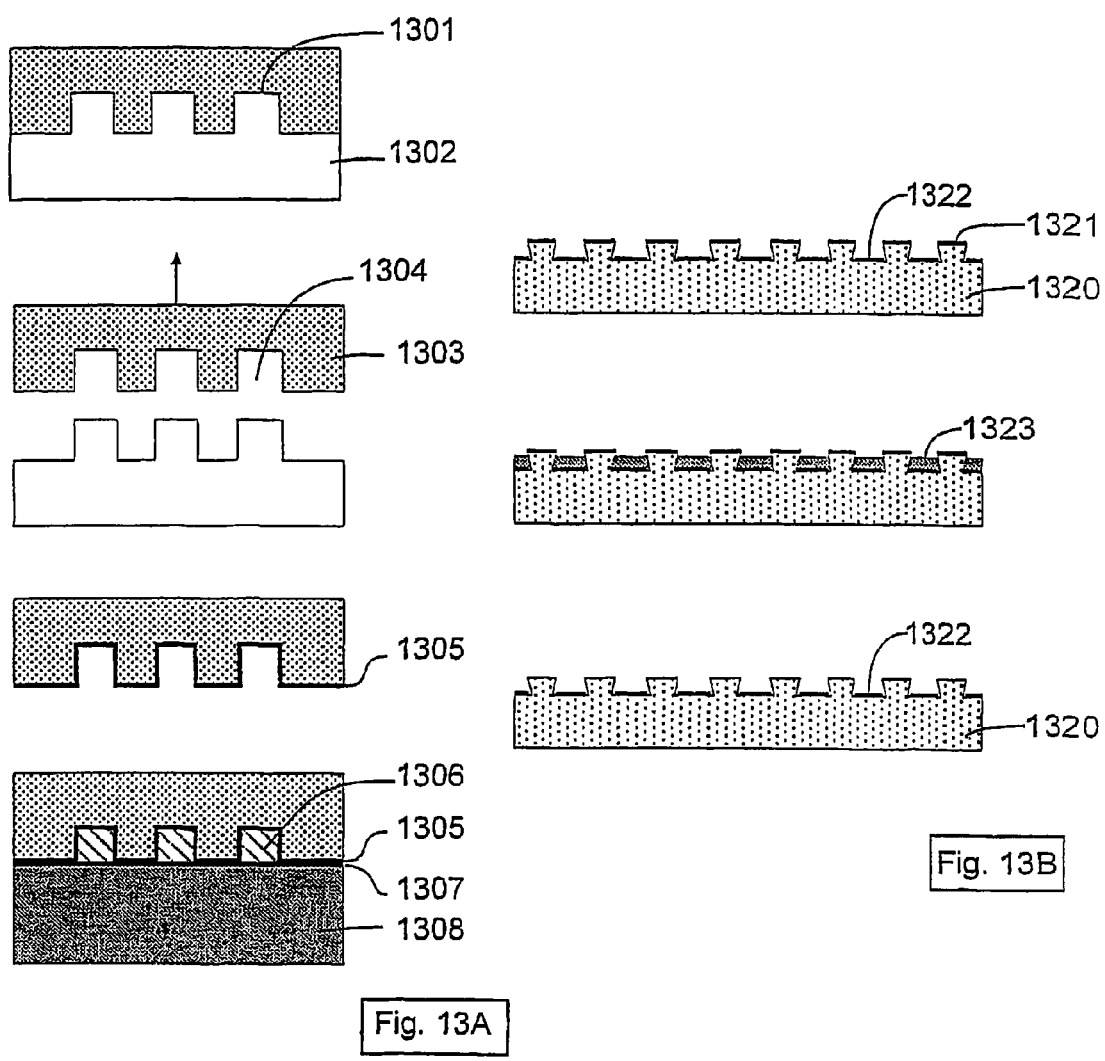
Figure 15B:
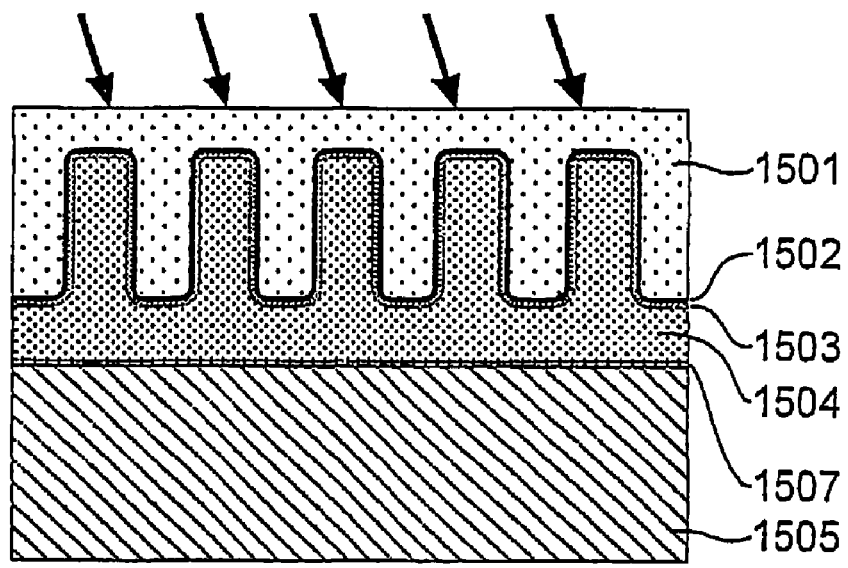
Figure 15C:
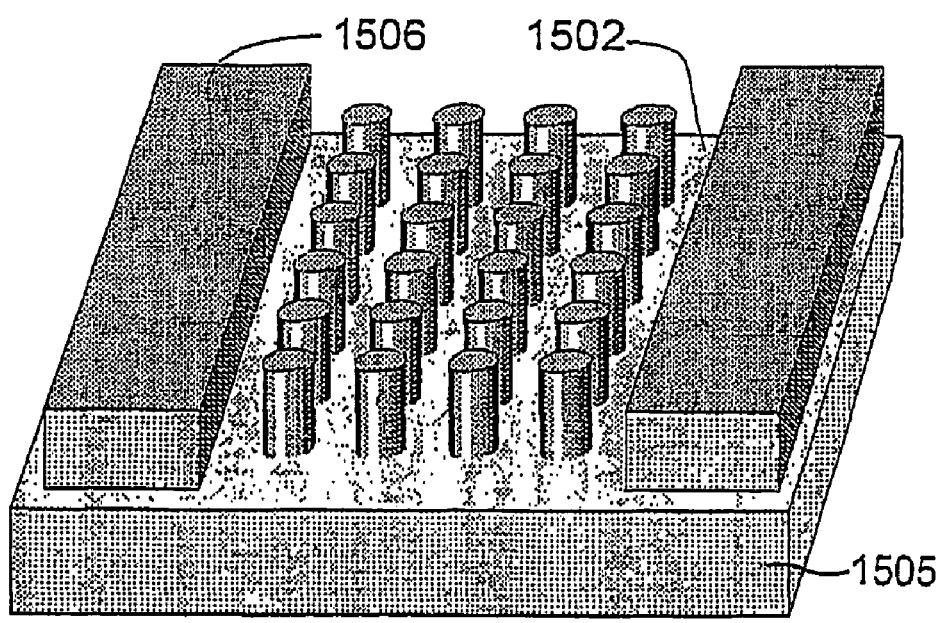
Figure 16:
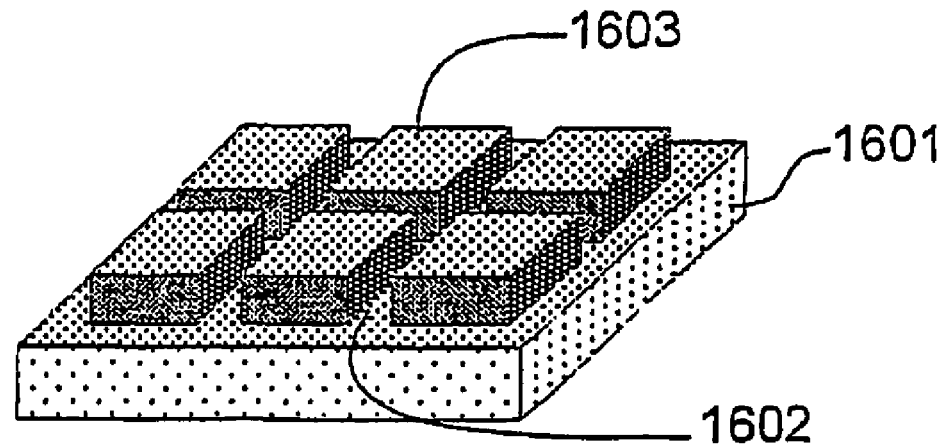
Figure 16:
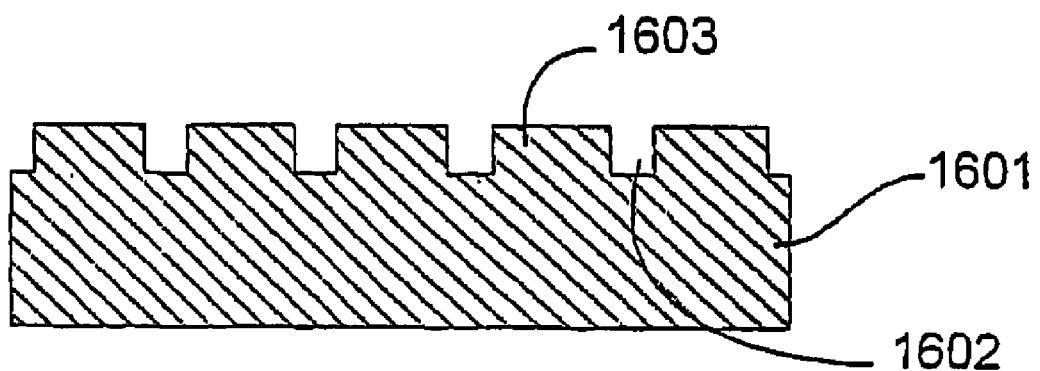
Figure 16:
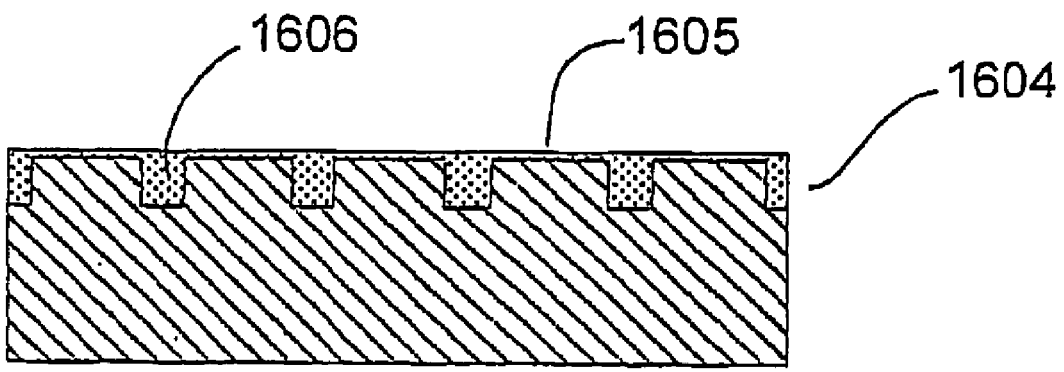
Figure 17A:
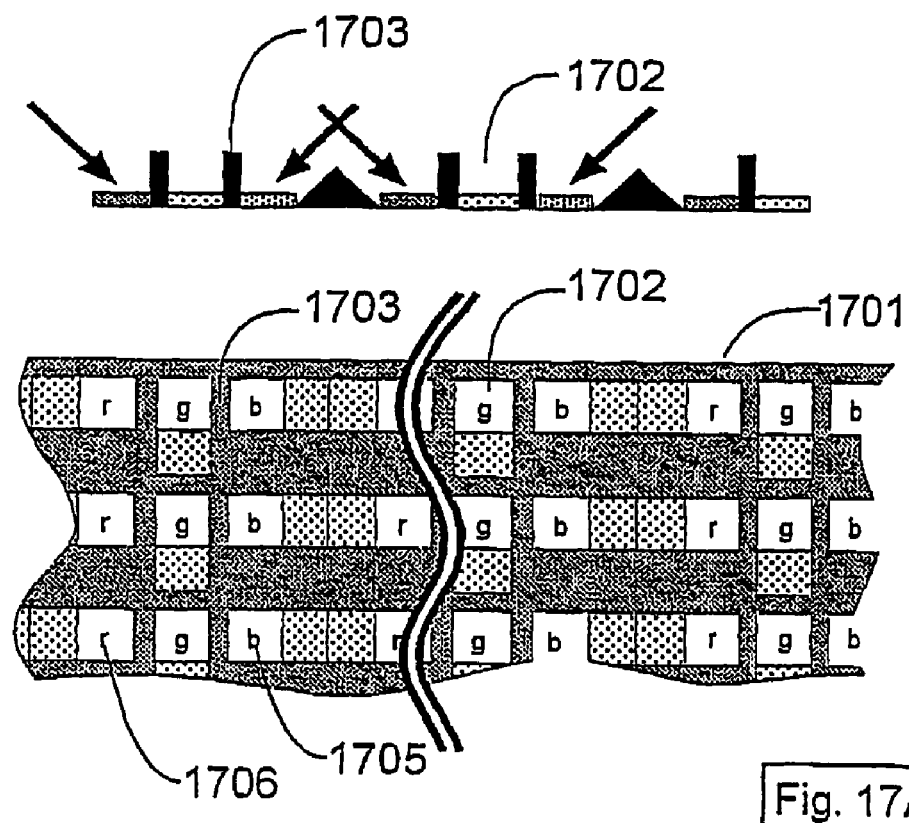
Figure 17B:
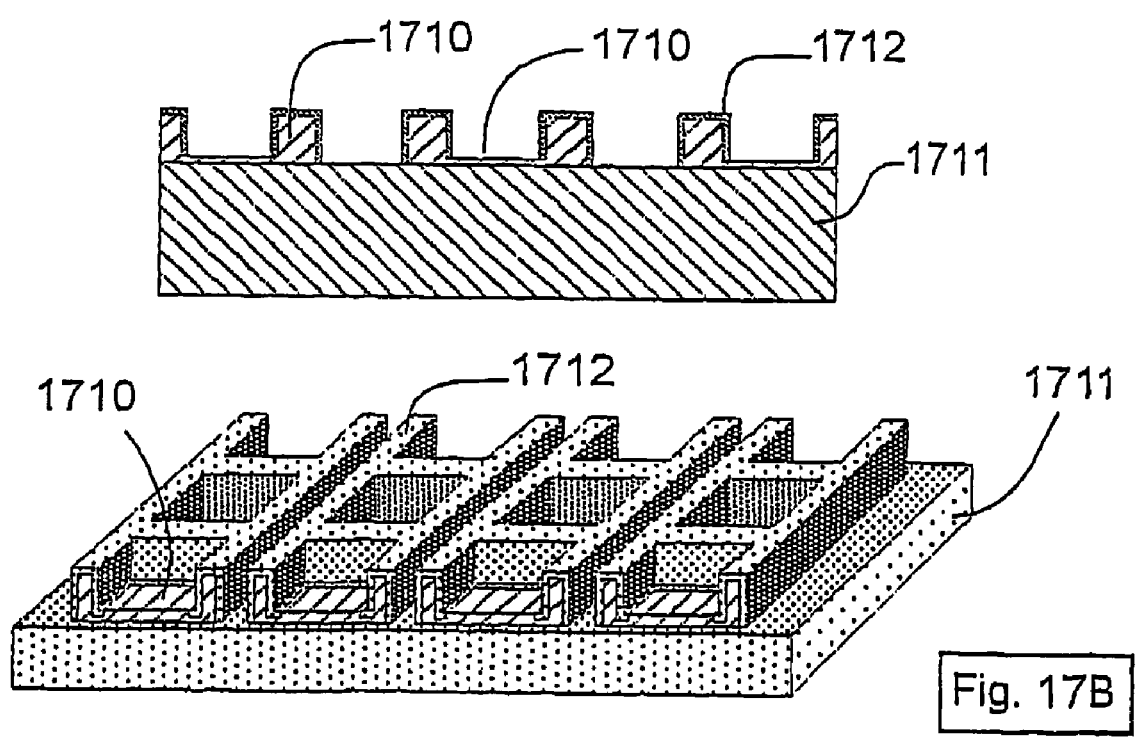
Figure 18:
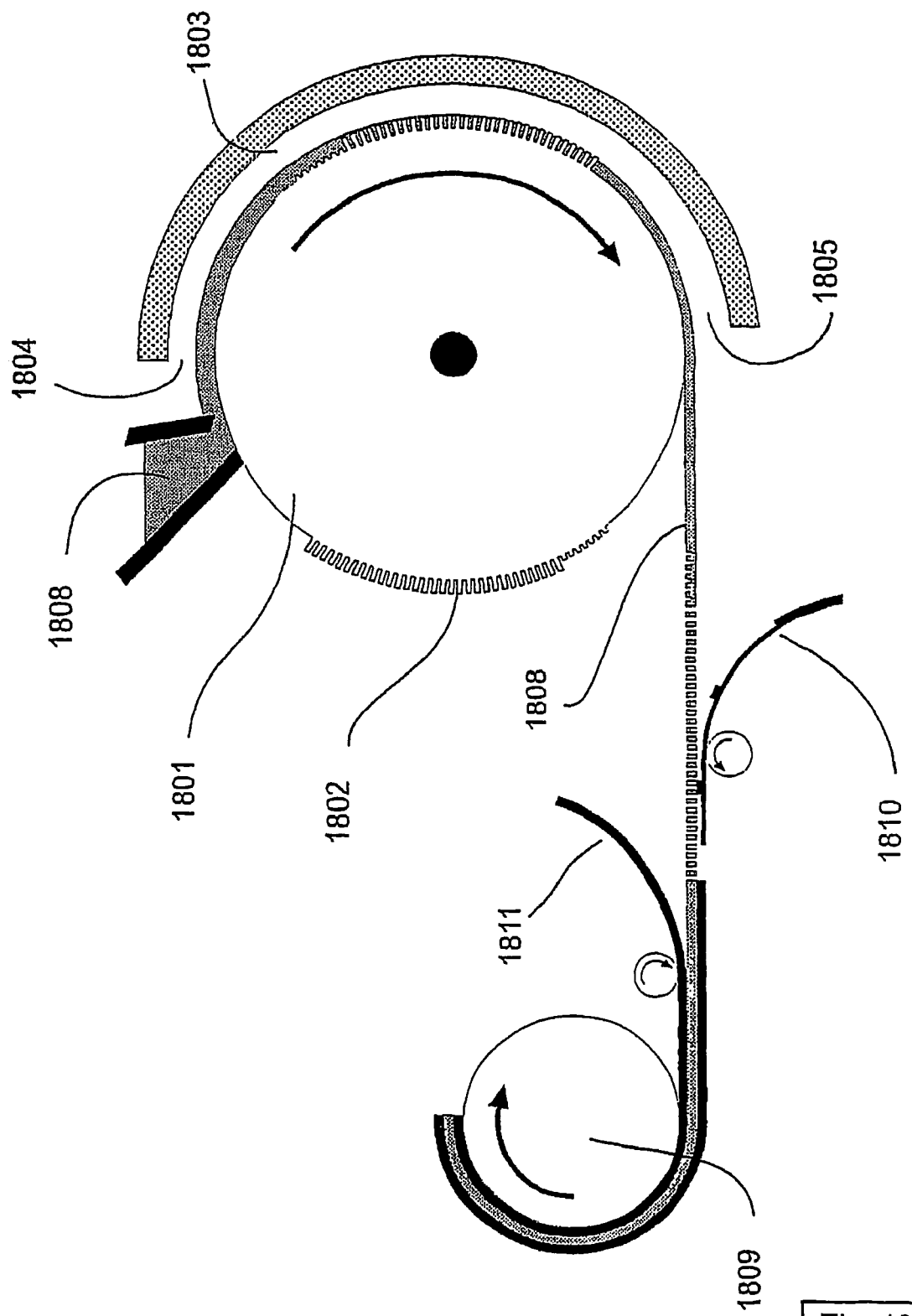
Figure 19A:
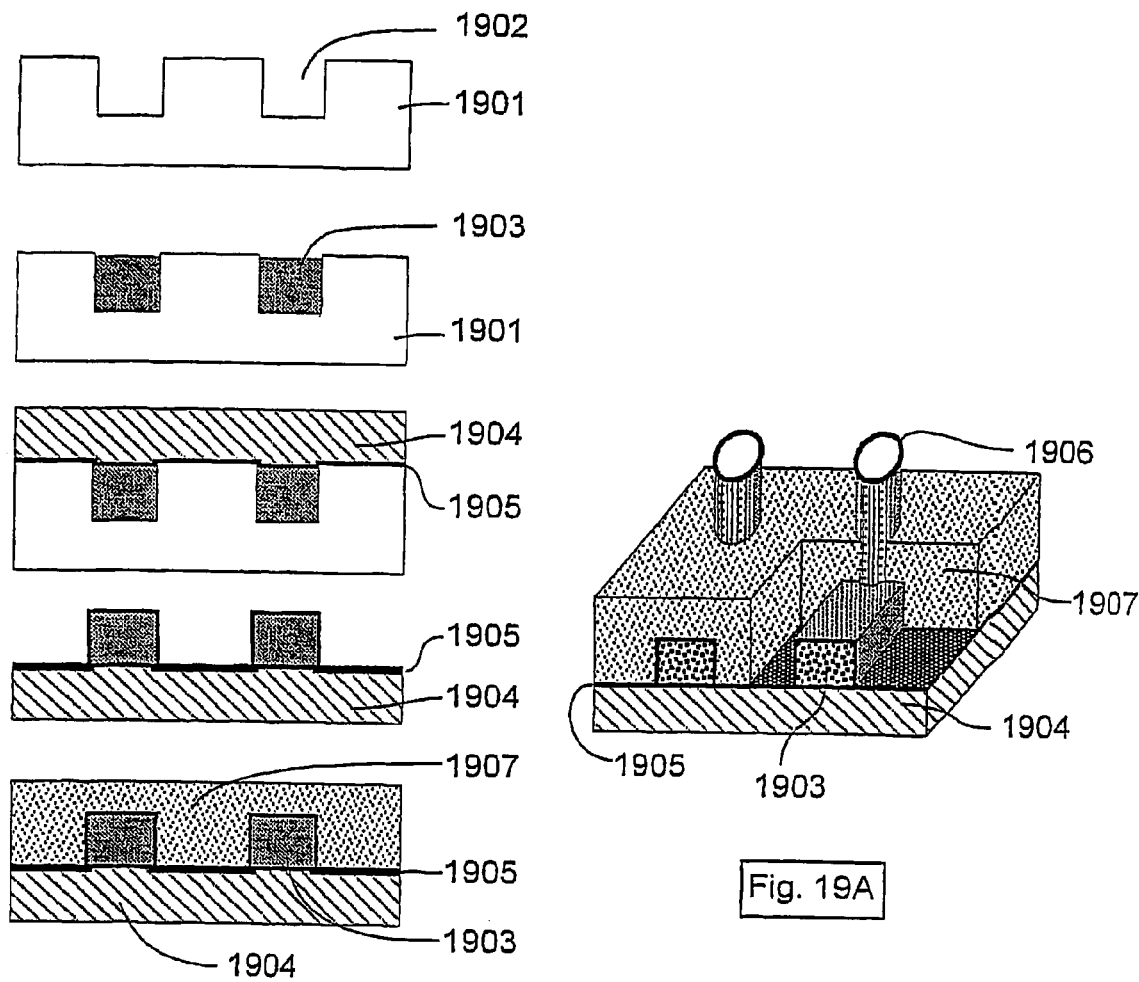
Figure 20A:
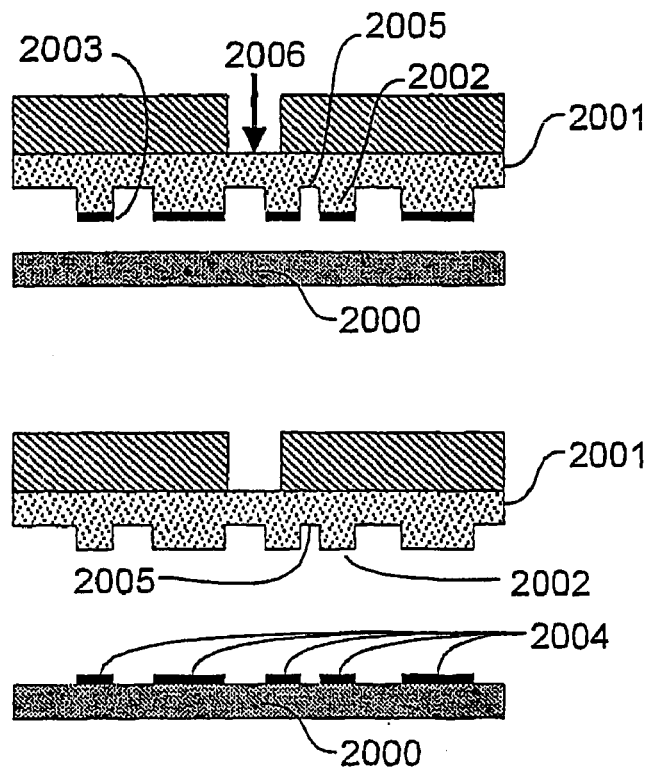
Figure 22A:
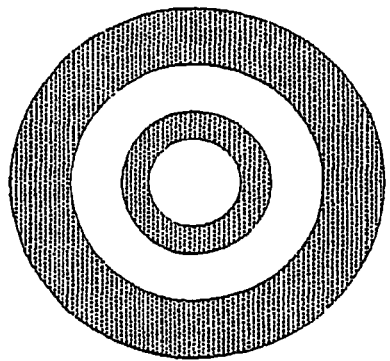
Figure 24A:
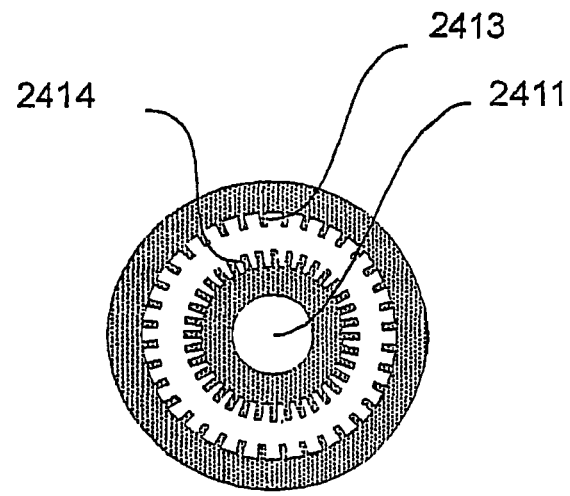
Figure 25:
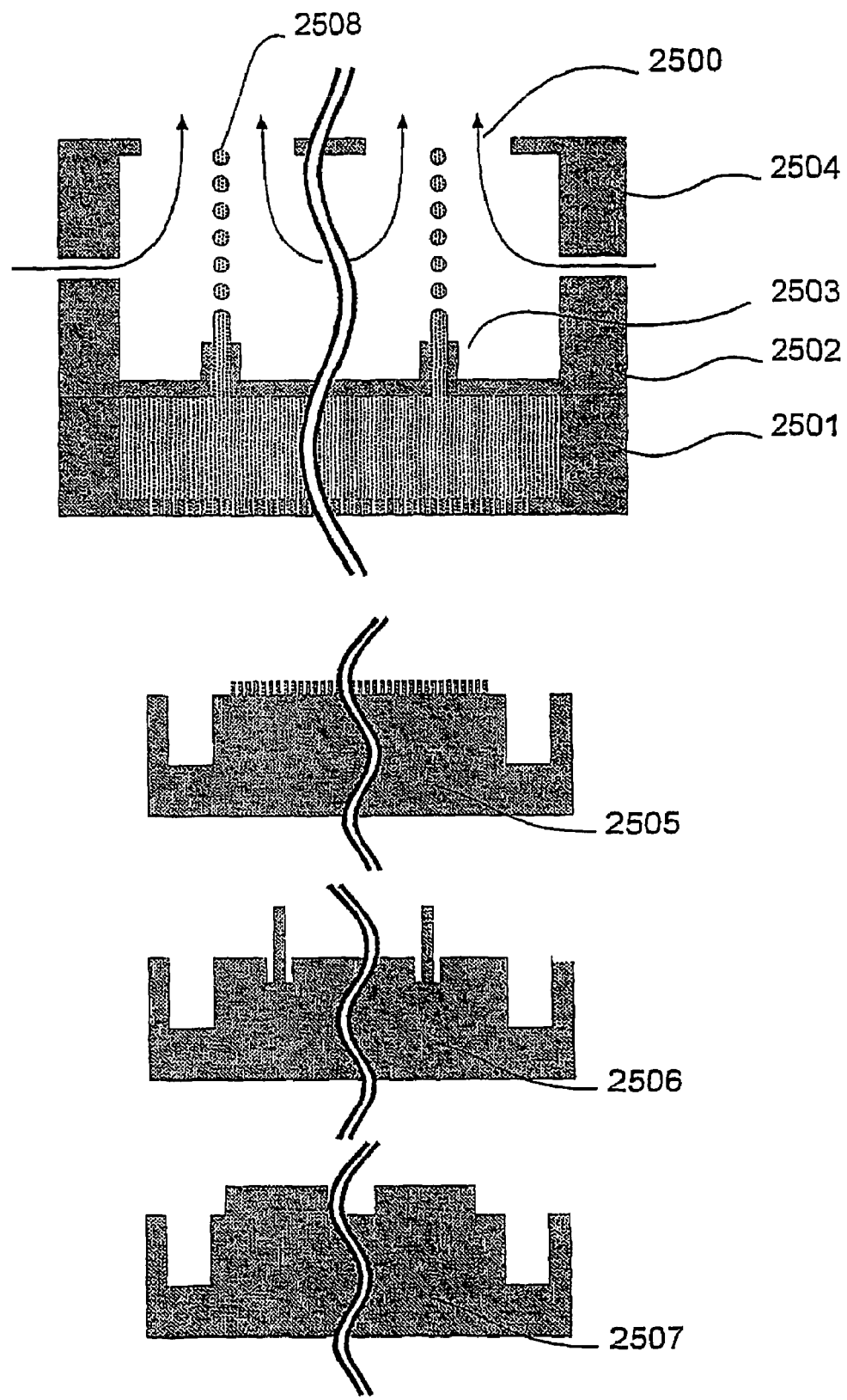
Figure 26:
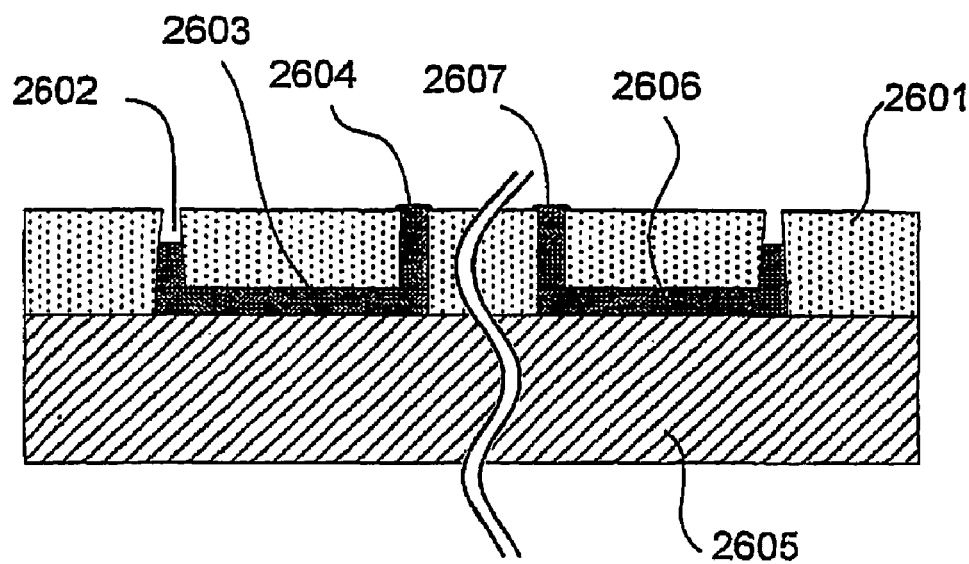
Figure 27:
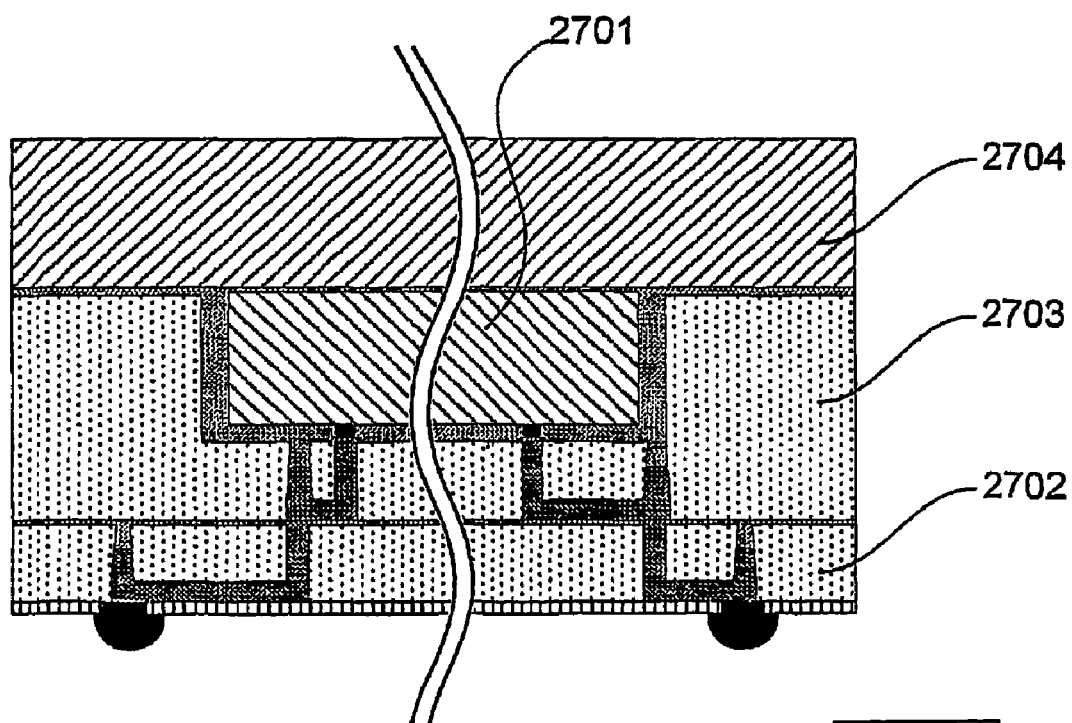

FIG. 11 shows a SEM picture of a top view of a micro array with 200 micron sized probe regions according to the invention, FIG. 12A shows a SEM picture of a carbon microsieve, FIG. 12B shows a SEM picture of an inorganic microwell structure, FIG. 13A shows process steps for obtaining an optical splitter FIG. 13B shows process steps for an optical grating, FIG. 14 shows a SEM picture of a top view of an optical splitter, FIG. 15A shows a SEM picture of a nanostructured photovoltaic device, FIG. 15B shows an embodiment of a photovoltaic device, FIG. 15C shows an 3D view of a photovoltaic device, FIG. 16 shows a transparent conductive board with a conjugated polymer, FIG. 17A shows a multicolour pixel display with a shadow mask technique, FIG. 17B shows a transparent conductive board for a pixel display, FIG. 18 shows a device for continuous production of e.g. polymeric fluidic boards, FIGS. 19A,B show different embodiments of an electrophoretic capillary board, FIGS. 20A,B,C, 21, show different embodiments of micro printing tools, FIG. 21B shows a SEM picture of a cross-section of a micro printing tool, FIGS. 22A,B show a cross section of a conventional spinnerets for membrane production, FIG. 23 shows a SEM picture of a cross-section of a micro structured membrane, FIGS. 24A,B show a cross-section of a spinnerets with a microstructure, FIG. 25 shows a nozzle device for atomisation, FIG. 26 shows a ball grid array, FIG. 27 shows a stack of grid array's connected to an electronic chip.

EXAMPLE 1

Moulding of a Microsieve with Vapour and Liquid Induced Phase Separation

A polymeric micro sieve 106 is made by casting a thin film 104 with a thickness of 40 micron of a polyethersulfone (PES) solution with the aid of a casting knife over a mould 103 having a large number of small orthogonal protruding cylindrical rods 101 with a diameter of 2 micron and a height of 8 micron on mesa's 102 with a height of 30 micron (FIG. 1). The polyethersulfone solution contains 3.75 g PES (BASF, Ultrason E 620p), 25 g N-methylpyrilidone (NMP) and 20 g acetone per 48.75 g. The acetone is a solvent with a low boiling point and the NMP is a solvent with a high boiling point. After the evaporation of the acetone and shrinkage of the casting solution for 10 seconds in a water vapour environment the mould together with the PES precipitate is immersed in a water bath at a temperature of 20° C. for 30 seconds which induces a further shrinkage of the casting solution 105. The NMP in the PES solution diffuses to the water bath while the water diffuses into the NMP-rich PES solution. The water is a non-solvent for the PES and phase separation is induced resulting in a microporous PES film still containing water and NMP in the pores. The resulting product 106 is easily released from the product and is dried at ambient temperature. A fast solvent exchange may first be applied by first washing with ethanol and subsequently hexane before further drying steps. This may be important when tie polymers used are rubbery and tend to collapse upon drying.

Figure 2:
FIG. 2 shows a SEM picture of a cross-section of a micro sieve.
Figure 3:
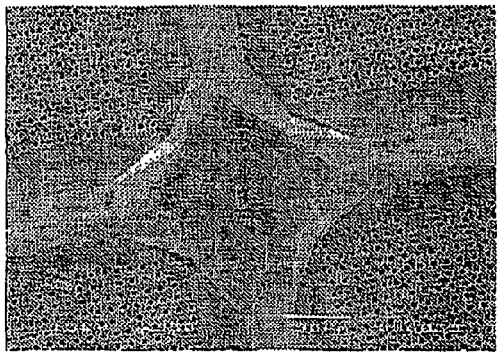
FIG. 3 shows a SEM top view of a supported microsieve.

Due to the shrinkage of the PES film partially by the evaporation of the acetone and mainly during the immersion in the water bath, a very thin (thickness 3 micron) crack-free microporous microsieve is obtained after the drying process. Due to the shrinkage of the PES solution the perforations (perforation diameter 6 micron) are somewhat larger than the diameter of the rodlike protrusions on the mould (FIGS. 2,3 show a SEM cross-section and a topview of the obtained supported microsieve). Using a higher initial polymer concentration the amount of shrinkage is reduced. The addition of surfactants (SPAN 80, TWEEN) might enhance the perforation through the rods 101 of the casting solution. Moulds with strong rods 101 have been made with nickel electroplating techniques from Stork Veco. A great advantage of the described technique is that the casting knife does not have to touch the mould during casting so that abrasion of the mould is negligible in time.

The microsieves can be made in a broad range 10 nm-10 micron of pore sizes and have been made with different phase separation techniques and many different polymers like polyimide, polypropylene, polyamide, Teflon®, polyurethane, bio and non-bio degradables, ceramics etc. Liquid induced phase separation is very well accomplished by immersion in an immersion bath, in which the concentration of the non-solvent in the bath is larger than 5% and preferably larger than 95%, in order to prevent the formation of thin and porous skin layers. Vapour induced phase separation is very well accomplished, in which the concentration of the non-solvent in the vapour is less than 25% and sometimes depending on the aspect ratio of the micro perforated structures, less than 1%. Vapour induced phase separation may be quickened, in that the non-solvent is already partially dissolved in the fluid with a concentration less than 2%, in above example with a water concentration of e.g. 0.6%.

Good results have been obtained with e.g. perforated and non perforated structures and a dense or open skin layer covering all aides of the product in that the casting solution contains at least two solvents in which a lowest boiling solvent and a highest boiling solvent have a difference in their respective boiling points of approximately 50° C. or greater; removing a predominant amount of said lowest boiling solvent by evaporation; contacting the solution with a non-solvent for the material, but which is miscible with said at least two solvents to induce phase separation and solidification; releasing the solidified product from the mould.

The Lowest boiling solvent is selected from the group consisting of tetrahydrofuran, acetone, 1,4-dioxane, 1,3-dioxolane, ethyl acetate, methyl ethyl ketone, cyclohexanone, cyclopentanone and mixtures thereof.

The highest boiling solvent is selected from the group consisting of dimethylformamide, dimethylacetamide, N-methylpyrrolidone, ethylene carbonate, propylene carbonate, glycerol and derivatives, naphthalen and substituted versions, acetic acid anyhydride, propionic acid and propionic acid anhydride, dimethyl sulfone, benzophenone, diphenyl sulfone, sulfolane, phenol, m-cresol, dimethyl sulfoxide, diphenyl ether, terphenyl, cyclohexanone, cyclopentanone and mixtures thereof.

Good results have been obtained with a non-solvent selected from the group consisting of water, methanol, ethanol, isopropanol, toluene, hexane, heptane, xylene, cyclohexane, butanol, cyclopentane, octane, higher alcohols, glycols and miscible mixtures of these non-solvents.

The monolithic microsieves may be used for e.g. beer and wine clarification, cold sterilisation of beer and milk, blood plasma filtration, leukocyte or plasma filtration, microbiological analytical applications, PolymeraseChainReaction probefilters, shadow masks for e.g. electronical applications, fotonic crystals, nano stencilling methods, micro contact printing, prefilters, mixers, as a tool to produce light emitting displays etc. The microsieves may be used without a support or with one or more supports. The obtained product may be elastomeric, non-elastomeric, piezo active, etc. depending on the chosen casting solution and the intended application (e.g. vibrating microsieves of piezo active PVDF for filtration and atomisation). Also reinforced nozzle plates for a variety of applications can be made such as ink jet printing, (cross flow) emulsification nozzles for the production of single, double and multiple emulsions, atomisation nozzles for fuel injection, and as an electrically insulated but perforated spacer (having e.g. an electrolyte or another medium within the perforations) for e.g. battery applications. Of coarse many other perforated articles such as encoder disks, micro and nano stencils for e.g. the evaporation of isolated magnetic domains, SAMs, and many other organic and inorganic materials can be made according to the invention.

EXAMPLE 2

Moulding of a Three Dimensional 3D Biocompatible Scaffold Product with Liquid Induced Phase Separation 3D porous tissue products are of importance e.g. in the regeneration of human skin, wound dressings, biodegradable tissue scaffolds and as implantable, semipermeable diffusion membranes for artificial organs such as for using pancreatic islets for release of insulin. The membrane allows bodily fluids to diffuse in and out of the membrane but prevents the movement of the subject's immune cells and antibodies into the membrane if the pore size is well below 50 nm. Retention of e.g. imnunoglobulin G requires pore dimension smaller than 20 nm.

It is well known that the diffusion of nutrients through the membrane is severely hampered if the thickness of the membrane exceeds 100 micron. It is an object of the invention to provide moulded reinforced filtration or diffusion membrane products with an adjustable mean pore size (e.g. less than 20 nm) in the skin layer and with a local mean thickness including the skin layer less than 100 micron. A polymeric reinforced filtration membrane 401 (FIG. 4) is made by casting a thin film of a polyimide solution with the aid of a casting knife over a mould having a large number of mesa's with a height of 300 micron and size 300×600 micron. The mean distance between the mesa's is 200 micron. The polyimide solution contains 3.75 g Matrimid 5218 polyimide (CIBA), and 25 g NMP per 28.75 g. The mould together with the polyimide precipitate is immersed in a water bath at a temperature of 20° C. for 60 seconds. The induced phase separation results in a microporous reinforced membrane 403 with a nanoporous skin layer with a mean pore size less than 20 nm on the immersion bath side. The mean thickness of the diffusion membrane between the struts 402 is 20 micron, well below the critical 100 micron diffusion limit. A stack of reinforced membranes 401 and microsieves 407 may be used for different applications. Reinforced struts 504 may be applied on the backside of the membrane 507 but reinforced struts 505 may also be applied on the frontside of the membrane (FIG. 5). A second moulding step shortly after partial evaporation of a solvent (partial solidification) of the casting solution but before the immersion step can be performed to obtain such double strutted structures. One or two porous micromoulds saturated with a non-solvent may also be used to obtain such single and double strutted structures. The construction of such porous moulds may be obtained according to the invention. Porous moulds made from e.g. Teflon or polypropylene are advantageous because they do not dissolve easily in most (non)solvents that are used in casting processes according to the invention. Reinforced biocompatible membranes 507 may be used e.g. for cell seeding, cell growth or cell encapsulation. Depending on the application a number of different membranes 507 and microsieves 508 may be stacked to provide e.g. cell encapsulation 509 chambers. Polyimide and polyurethane are well known for its strength. and have biocompatible non-biodegradable properties.

A bio degradable membrane is made by casting a film with a thickness of approximately 500 micron of a block-copolymer polyethyleneoxyde/polybutylenetere phtbalate (PEO/PBT, 80/20, 1000 gr/mol) dissolved in chloroform with the aid of a casting knife over a mould having a large number of mesa's with a size of 500×500 micron and a height of 300 micron. The distance between the mesa's is 300 micron. Ethanol is used as an immersion bath to induce phase separation. A mean membrane thickness between the struts 604 of 50 micron is obtained after drying (FIG. 6). A vacuum process is applied to remove all solvent residue and a ethyleneoxide treatment may be given for sterilisation.

The casting solution may also comprises solid, e.g. added nondissolved salt particles that can be leached out of the product after phase separation, to create 3D macroporous (>5 micron) structures.

According to the invention 3D scaffolds with large spaced lamellae or fibres 605 (zigzag stacking) may be provided with a moulded microsieve foil (e.g. pore size 1-50 micron) 607 to create separated chambers to enable growth of different cells in different chambers, or to create an anisotropy in the 3D scaffold for other purposes. The fibres may also be obtained according to the invention with an 3D extrusion nozzle having a microstructire to provide the fibres with grooves and ridges 608 along the fibre to promote cell attachment The extruded fibres (or other structures) themselves may also be made in combination with a phase separation process to obtain uni or bimodal pore size distributions for enhanced cell growth and interdiffusion of bio liquids. FIG. 7 shows a SEM picture of such a bimodal construct.

Biodegradable materials may be used for similar moulding phase separation methods to obtain products of materials like e.g. aliphatic polyesters, polyetheresteramides, ethylenevinylacetates, polyanhydrides, polyorthoesters, polymers of lactic acid and glycolic acid and alphahydroxyacids, polyphosphazenes, protein polymers like albumin or collagen, polysaccharides and polylactide-co-glycolide. Aliphatic polyesters can be homopolymers, copolymers (random, block, segmented, tapered blocks, graft, triblock, etc.) having a linear, branched or star structure. Preferred are linear copolymers and block copolymers from the family of polyethyleneglycol (oxyde/terephthalate) and polybutylteraphtalate (PEG/PBT, PEGT/PBT, PEO/PBT all related to Polyactive®) for its biodegradable and biocompatible properties. Suitable monomers for making aliphatic homopolymers and copolymers may be selected from the group consisting of, but are not limited, to lactic acid, lactide (including L-, D-, meso and D,L mixtures), glycolic acid, glycolide, epsilon-caprolactone, p-dioxanone (1,4-dioxan-2-one), trimethylene carbonate (1,3-dioxan-2-one), delta-valerolactone, beta-butyrolactone, epsilon-decalactone, 2,5-diketomorpholine, pivatolactone, alpha, alpha-diethylpropiolactone, ethylene carbonate, ethylene oxalate, 3-methyl-1,4-dioxane-2,5-dione, 3,3-diethyl-1, 4-dioxan-2,5-dione, gamma-butyrolactone, 1,4-dioxepan-2-one, 1,5-dioxepan-2-one, 6,6-dimethyl-dioxepan-2-one, 6,8-dioxabicycloctane-7-one, polyetheresteramides and combinations thereof.

Other "biocompatible" materials (bio and non bio-degradable) can also be used for various biomedical applications as polystyrene, polyglycolide, poly acrylate, polymethylmethacrylate, polyhydroxyethylmethacrylate, poly vinyl alcohol, polycarbonate, polyethylene-co-vinylacetate, polyanhydride, polyethylene, polypropylene, polyhydroxybutyrate, polyhydroxyvalerate, polyurethane, polyetherurethane, polyesterurethane, polyarylate, poly anhydride-coimide, polyaminoacids, polyphosphazene, chitosan, chitin, celluloseacetate, cellulose-nitrate, nylon, polycarbonate mixed sters. 40/60 psilon-caprolactone-co-(L)lactide copolymer film.

Many other materials are described by Allcock in The Encyclopedia of Polymer Science, Vol. 13, pages 31-41, Wiley Intersciences, John Wiley & Sons, 1988 and by Vandorpe, Schacht, Dejardin and Lenmiouchi in the Handbook of Biodegradable Polymers, edited by Domb, Kost and Wisemen, Hardwood Academic Press, 1997, pages 161-182.

Products with topographic features corresponding to cellular dimensions (1-100 micron range) cells seem to exhibit enhanced cellular attachment and orientation and a more in vivo like cellular morphology (fibroplast attachment and induce contact guidance of these cells) topographical, spatial chemical and immunological control over cells to create functional tissue engineering constructs. A number of different products may be stacked onto each other to create isotropic and anisotropic features for e.g. wound dressings and other scaffolds. A wound dressing according to the invention may be provided with e.g. channels (e.g. diameter 5-100 micron and a length up to a few mm) for directional growth of blood vessels and nerve cells. Next stacked products for a wound dressing or other applications may have similar features with smaller dimension. The last stacked product may have only microporous features for e.g. oxygenation and anti bacterial purposes. Coatings like e.g. laminin may be used to promote cell attachment. Biodegradation time of products according to the invention may be altered by changing the porosity and the pore size of the product. Products may be made with a relatively dense and smooth skinlayer. Products without a skin layer show an intrinsic micro roughness which is advantageous for promoting cell adhesion and the like. Products with a connected cell morphology have the advantage for an enhanced interdiffusion of bioliquids. Products according to the invention may itself also be used as a sacrificial mould for bio and non bio degradable materials like polymers for tissue scaffolds and ceramic slurrys (e.g. hydroxyapatites) for bone replacement. The sacrificial mould may be dissolved in a suitable selective solvent for polymeric constructs or pyrolised for ceramic constructs. The tuned micro roughness of the sacrificial mould (with or without a skin layer) according to the invention and with functional microstructures will always be transformed to the product.

Products with embedded microstructures according to the invention can be folded to a tube examples of which include a artificial tube for nerve, artificial tube for spinal cord, artificial esophagus, artificial trachea, artificial blood vessel, artificial valve or alternative medical membranes such as artificial endocranium, artificial ligaments, artificial tendons, surgical sutures, surgical prostheses, surgical reinforcement, wound protecting materials, artificial skin and artificial cornea. FIG. 8 shows an example of a folded tube 801 made from collagen with channels 802 having a cross section of 20×20 micron for directional cell growth and interconnection of two nerve ends 803.

EXAMPLE 3

Moulding of a Micro Array for Proteomic and Genomic Applications, Microwells and Micro Titration Plates On a microarray, a plurality of regions (called features) are defined on which different probes e.g. nucleic acids, amino acids, oligonucleotides, antibodies, antigens, etc. are immobilised. The microarray is placed into a reaction container together with a sample e.g. DNA or the like to allow e.g. fluorescence-labelled sample DNA to hybridize with the probes immobilised on the respective features of the microarray. Thereafter, the microarray is irradiated with excitation light to measure fluorescent intensity of each feature. Based on the measured fluorescent intensities, the binding levels between the respective probes and the sample DNA are obtained and converted into desired information.

Probes can conveniently be applied with ink-jet technology on solid supports such as glass slides or porous supports like nitrocelluse, polyvinylenedifluoride, polypropylene, polysulfone and nylon. Ink-jet technology also allows for the accurate deposition of defined volumes of liquid. On porous products often splattering (diffusion) of probes is observed, a problem that increases with the goal towards more densely packed array probes. Porous products with orthogonal pore channels may be used (like Inorganic Anopore membranes, Whatman, Pamgene) to inhibit splattering. Another method is to provide a grid of hydrophobic material on the porous product (Abouzied, et al. 1994), or laying down stripes of an uncured or otherwise flowable resin or elastomer solution and allowing the material al least partially to infiltrate the porous array product to prevent splattering. According to the invention other (polymeric) micro array structures are more suitable in order to prevent splattering especially in view of the need for further densification of probe spots. First of all polymeric phase separation techniques may be employed to provide more orthogonal directed pore channels like macrovoids in the porous product. Orthogonal oriented macropores can be made with PMMA/butylacetate as material/solvent and n-hexane as a non-solvent. Added surfactants in general (e.g. TWEEN 80) may also influence the forming of orthogonal channels.

Secondly a mould may be used for heat-seal stamping of the porous support which seals locally pores and forms a water-impervious barrier between different probe regions. This mould may also be used for cold seal stamping during or short after a phase separation process to obtain porous and dense areas. A microporous mould saturated with an alcohol or glycol (delayed mixing) may also be used to pattern locally regions with a very thick skin layer. Thirdly phase separation is used to obtain porous mesa's (probe regions) with a grid of thin and deep gaps between the different probe regions. Fourthly moulding may be employed to obtain micro well structures in which the walls of the well are microporous but provided with a dense skin layer and the bottom of the well is microporous and lacking this skin layer. The different probes may be then e.g. deposited in different wells and the probe material will then mainly be absorbed by the bottom of the well. A surplus of probe material will then be more absorbed by the microporous walls of the well via the bottom of the well without a skin layer (FIG. 9B). Such products may easily produced by using a mould in which the different parts have different phase separation conditions. Fifthly the moulding may be accomplished in two steps. Step one entails the formation with e.g. phase separation of a dense or hydrophobic grid/multiwell structure 1001 with chambers 1002 and step two entails the filling of these chambers 1002 with a phase separation process with a microporous probe binding material 1003 (FIG. 10).

The filling of these chambers 1002 with the phase separating material may be done with inkjet printing together or sequential with the probe material 1003. The filling may also be done by normal phase separation casting techniques especially when using a fully perforated grid. The material of the grid may be dense, hydrophobic and/or microporous with a closed cell structure (non-connecting pores). After applying a casting film for phase separation e.g. with a thickness of 20 micron on a grid 1001 with a thickness of e.g. 10 micron, due to the large shrinkage of this film during precipitation in the non-solvent bath, the microporous polymer (with an open cell structure/connecting pores) will mainly reside within the perforations of the grid. The material of the grid 1001 may be e.g. polymeric or ceramic. The grid 1001 may be microporous and a treatment may be given to fill or to make it hydrofobic before the filling of the chambers 1002. Preferentially the walls of the chambers 1002 are tapering and/or have a sufficient micro roughness to lock the probe material 1003. A number of different hybrid microarrays have been manufactured with polyvinyldifluoride (PVDF) and polypropylene as a grid material and respectively nitrocellulose, PVDF and nylon as a probe binding material 1003. FIG. 11, shows a SEM picture of a topview of a micro array with 200 micron sized probe regions according to the invention. Of coarse many other combinations of grid and probe binding materials as well as dimensions are possible.

The thickness of the hybrid or non-hybrid microarray film is preferably between about 10 and 100 micron. In order to improve alignment of the microarray/well plate with a suitable probe filling device alignment marks can be provided in the product. Also the distance (e.g. 5 micron) between the different probe regions can be made as small as possible with respect to the size of the probe regions e.g. 100 micron), which is easily possible with high aspect ratio structures. Without alignment techniques the probe material can also be deposited in more than one multiwell, provided that the different multiwells have a size (e.g. 2 micron) are much smaller than the probe spot (e.g. 20 micron). In a preferred embodiment, ach microarray contains about $10^3$-$10^8$ chambers 1002 for $10^3$-$10^6$ distinct polynucleotide or polypeptide biopolymers per surface area of less than about 1 $cm^2$. Also in a preferred embodiment, the biopolymers in each microarray region are present in a defined amount between about 0.1 femtomoles and 100 nanomoles and each probe region has an imprinted determination-code originating from the used mould. The ability to form high-density arrays of biopolymers, where each region is formed of a well-defined amount of deposited material, can be achieved in accordance with the microarray-forming method described.

Products according to the invention may also be used to manufacture dense/microporous micro well and titration plates, preferably provided with a identification or bar code per well or titration section. FIGS. 9A,9B show SEM pictures of microporous micro multiwell plate structures of a hydrophilic polyethersulfone/polyvinylpyrrolidone for e.g. cell encapsulation and to study cell growth. Feeding solutions can easily be applied through the microporous material. Different surface sections may have different surface morphologies (with or without a locally smooth skin layer) depending on the exact liquid-liquid demixing and liquid-solid demixing conditions during phase separation.

A micro moulded multiwell plate of polystyrene was made by thermally induced phase separation. Polystyrene (Dow) was dissolved in diisodecylphthalate (Merck) to a 23 wt % casting solution and heated to a temperature of 120° C. With a casting knife the solution was cast 300 micrometers thick on a mould with a cylindrical pillars with a diameter of 5 micron and a height of 30 micron. Both the casting knife and the mould had a temperature of 120° C. The solution has gradually cooled down to a temperature of 20° C. and a porous layer has been formed at the imprint side of the structure, as seen by electron microscopy. Alternatively the solution has been cooled down very quickly in a water bath of 20° C., leading to a dense skin layer on the moulded and top side of the structure. Afterwards, the polystyrene multiwell plate was rinsed in ethanol.

EXAMPLE 4

Carbon, Inorganic and Conjugated Polymeric Microstructures

Carbon microstructures can be applied in a variety of applications such as arrays of interdigitated electrodes or capacitors, as electrode materials in a large variety of analytical and electrochemical applications, particularly sensor applications, as electrically actuated cantilevers, sample holder grids for scanning electron microscopy as well as electrodes, and current-collector plates in fuel cells.

A micro-moulded substrate obtained by phase separation may be prepared specifically for further processing into glassy carbon microstructures with micro to nanometer sized geometric features. Such subsequent processing generally comprises the carbonisation of the polymeric micro-moulded substrate by a controlled heat treatment. The carbonised micro-moulded substrate may also be functionalised after the heat treatment by for example chemisorption, physisorption, wash-coating, deposition methods such as chemical vapour deposition, plasma deposition, sputtering, precipitation, and photolithographic add-on methods.

A micro sieve produced according to example one is carbonised under well-chosen conditions to avoid buckling or cracks resulting from anisotropic shrinkage and residual stresses during carbonisation. Between the micro-moulding of the substrate and the carbonisation, the substrate was not functionalised. Shrinkage of the substrate occurs to an extend of approximately 60%. The observed shrinkage is uniform in both the support and the perforated structure. The extent of this shrinkage however depends strongly on factors such as the porosity of the micro-moulded substrate, the pyrolysis procedure, temperature ramp rate and residents time at intermediate and end temperatures, the material of the substrate, and the atmosphere in which carbonisation occurs (inert or oxidative). The choice of the preparation conditions during phase separation influences the porosity. The material forming th micro-moulded substrate determines the maximum carbon yield. Materials to be processed in the present invention can be for example aromatic polyimides, polyacrylonitrile, polyetherimides, polyfurfural alcohols, phenolic resins, and polyvinyl chloride.

A carbon microsieve produced from a PI Matrimid 5218 substrate.

A PI Matrimid 5218 microsieve substrate was prepared following the procedure described in Example 1. This substrate was subsequently carbonised using the following the pyrolysis program: the substrate heated to 150° C. at a rate of 50° C./min and kept at this temperature for 15 min, subsequently the temperature was raised to 350° C. at a rate of 5° C./min. The final temperature was reached with a temperature ramp of 1° C./min. The end temperature was held for one hour, after which the microsieve was allowed to cool in the oven to ambient conditions. The resulting carbon microsieve can be seen in FIG. 12A.

Instead of having smooth carbon surfaces, one may desire to have a highly porous carbon network build up by nanometer-sized fibres with an large internal area acting as surface for electrochemical or catalytic reactions. It is also wishful to have such large internal surfaces inside miniaturised fluidic channels and assemblies. Such carbon networks with porosity's up to 90% still having considerable mechanical strength can be prepared by growing carbon nanotubes. However, to introduce a three-dimensional microarchitecture a heat resistant ceramic substrate is desired.

A particular version of the invention is a ceramic product prepared by a phase inversion process on a microstructered mould. The solution to be cast onto the mould may comprise a solvent or a mixture of solvent, a polymer or a blend of polymers, ceramic particles, low molecular weight additives and in some cases a non-solvent or a mixture of non-solvents. According to the invention, phase separation occurs shortly prior to casting or on the mould. The resulting product is a microstructured polymeric product containing ceramic particles. After drying of the product, it will be fired to remove the polymer leaving behind the ceramic particles. These may transform during the firing into a different ceramic or different crystal form. Firing causes the particles to agglomerate into a solid ceramic product having the microarchitecture of the polymer-ceramic precursor.

The ceramic microstructured product is heat resistant and can be further used to prepare carbon nanotube architectures. First, noble metal clusters are deposited onto the surface. Precipitation of nickel nitrate and subsequent thermal reduction serves this purpose for example. The microstructured ceramic product coated with Ni-clusters can be covered by carbon nanotubes subsequently. For this, the Ni-covered substrate is exposed to an reactive gas atmosphere of hydrogen diluted methane at ambient pressure and temperatures around 550 C. Depending on the length of the reaction, the carbon nanotube networks grows onto the microstructured product Inorganic Micromembrane A micromoulded ceramic membrane is made from a casting solution of polyethersulfone (ICI 5200 P) (5.8 wt %), NMP (19.8 wt %), acetone (15.6 wt %), and AlOH powder (Boehmite K30)(58.8 wt %). This was casted with a casting knife on a mould to form a 50/150 micrometer thick film. Part of the solvent was evaporated for 30 seconds, after which the film was immersed in a water bath. The micromoulded PBS film, containing the AlOH was put in an oven and heated up to a temperature of 600° C. with a speed of 35° C./min. In the oven there was a constant air flow of 1 l/min. After two hours at 600° C. the oven gradually cooled down to room temperature. FIG. 12B shows a SEM picture after sintering.

Carbon and inorganic microstructures may be used for specific operations in the analysis or synthesis of a sample at elevated temperatures. For example, the devices may include high throughput reaction chambers for performing synthesis, amplification or extension reactions.

Conducting Conjugated Polymeric Microstructured Electrodes

Products according to the invention can be used to fabricate 3D microstructured electrodes with enlarged active surface area to improve the efficiency. 3D Microporous products can be used to fill the micro pores with a suitable conjugated polymer like polyanniline, polypyrrole, PEDOT, etc. Products can also be used as a sacrificial mould for 3D structuring of conjugated polymeric electrodes. Such electrodes can easily be made by well known e.g. electrochemical polymerisation methods for e.g. battery applications.

Advantages of 3D electrodes are a denser packing thereby enabling a greater degree of interchain electron and proton transfer and an improved electrical charge storage capacity. Applications are, general polymer battery electrodes, particularly flexible thin-film battery, electrochromic devices, novel amperometric enzyme-entrapped conductive polymer electrode for biosensor applications (e.g., glucose sensor), and microelectronic or molecular-electronic devices. Also convective ion transport for e.g. ion-exchange and electro-dialysis membranes is improved by microstructures. Typical dimensions of the microstructure are multiple micron or submicron, substantially identical micro protrusions, wherein each protrusion has a height of between about 0.05 and 50 micrometers and a top surface area of up to about 0.0025 and 2500 square micrometers of conductive polymer on top of and in contact with a substantially smooth electrically conducting surface.

EXAMPLE 5

Wave-guide Structures

The introduction of new types of interactive multimedia services has increased the requirement for a substantially increased capacity on existing telecommunication network infrastructures, which is impossible to achieve without a wide use of fibreoptics in connecting, transporting, accessing, and in system equipment. Waveguide technology at a low cost is one of the most important regions which should be able to contribute to the breakthrough for optical solutions. Up to now silicon on silicon generally has been used as a waveguide material in telecommunication applications. A complete accomplishment of a low cost and a large volume scenario, however, requires the introduction of only low cost processes in a few steps, which only could be realised through the use of polymer materials.

An optical waveguide is formed when a dielectric material of refractive index n1 is placed between another dielectric material of refractive index n2, where n1 is greater than n2. On entering the guide, because of the difference in the refractive indices, the light is repeatedly totally internally reflected and travels along the path of the guide. In this way light is transmitted from one point to another.

There are two types of optical waveguides: a planar type optical waveguide and a channel type optical waveguide. A planar type optical waveguide has a portion through which light is guided (core) formed in a plane, while a channel type optical waveguide has a core formed as a channel. That is, in a planar type optical waveguide, the light is constrained in one direction, while in a channel type optical waveguide, the light is constrained in two directions. In this way, light can be transmitted even if the guide is curved. Other methods for producing optical waveguides using organic materials include selective removal of a thin film using either a laser beam, reactive ion etching (RIE), or wet etching.

One method which shows promise for low cost mass production was reported in "Fabrication of Low Polymer Waveguides using Injection Moulding Technology", Electronics Letters, 1993, Vol. 29, No. 4, pp. 309-401. In this method, a patterned product on which patterns of a groove constituting a capillary is formed by injection molding using a polymer material. This product is then used to form a channel type polymeric optical waveguide.

According to the invention many types of moulded waveguide products for optical linear and nonlinear, e.g. switches, splitters, WDM filters, phased arrays, Mach Zehnder interferometers, connectors, graded fibres, electrooptical devices, dense wavelength division multiplexers, optical pumps and multi array scanners can be made.

The products obtained by phase separation can be made or filled with a broad variety of materials like polymethylmethacrylate, polycarbonate, (benzo) cyclobutane, (thermoresistant) polyimide, poly(perfluorocyclobutane), polycyanate, rare earth polyfiner materials such as, erbium ($Er^{3+}$) doped (fluorophosphinate) polymers, and fluorine substituted versions hereof to diminish internal optical absorption. The used polymers may exhibit electrooptic, acoustooptic, magnetooptic or thermooptic effects or else optical fluorescence and stimulated emission (optical amplification).

Nanoporous (poresize <50 nm) products may be optically transparent and may be used as a cladding for the optical core. Microporous non-transparent products may first be provided with an appropriate cladding layer by means of e.g. dipping, spincoating, spray coating and the core layer may subsequently be applied by casting, capillary filling etc. The core layer may also directly be provided in a (sacrificial) product with a smooth skin layer and a rigid topplate with cladding properties, the product is then dissolved in an appropriate solvent in such a way that the core layer attached to the rigid topplate remains, and finally the core layer is provided with an additional cladding layer. It is clear that sequential processes are used with respect to the solvability of each of the used materials. Monomeric solutions may also be used and subsequently polymerised. Photoetchable optical materials have also a clear advantage in the construction of local optical devices within the product. Other parts of the product may of coarse be used for other functions e.g. microfluidic purposes.

The pores of the microporous moulded product can be filled and/or closed with another material, e.g. with a good thermal conductivity.

Products may first be provided with an electrical conductor like a metal (e.g. electroless plating or sputtering) or a conductive polymer (e.g. dip, spray or spin coating) with e.g. a specific resistance less than or equal to 10 power 10 ohm-cm. Such products have smoothened structures and may be used for electro optical devices. After filling an applied electric field by means of mounted electrodes may permanently crosslink the material in a polarised state.

FIG. 13A shows one embodiment according to the invention for the fabrication of an optical splitter. A mould 1302 with ridges 1301 having a cross-section of 50×50 micron has been casted with a PVDF polymer dissolved in a NMP/acetone solution according to the invention. After a LIPS phase separation in a water bath the nanoporous optical transparent product 1303 with rectangular grooves 1304 is dried. The product 1303 may be used directly as a cladding product and may be filled with a suitable optical core layer with a higher refractive index than the product. With preference the product 1303 is first provided with a thin cladding layer 1305 by dip, spray or spin coating, in this example with a PM coating (e.g. dissolved in a acetic acid/acetone solution) with a refractive index of 1.51 with a thickness of 1-3 micron. Next a core layer 1306 of with a refractive index of 1.52 is being casted with a casting knife in the dipcoated grooves 1304. Finally a second cladding layer 1307 of PMMA is being coated on the product and the core layer 1306. In a preferred embodiment the product 1303 is first closed with a cover plate 1308 having a cladding layer 1307 and next the core layer 1306 is being deposited in side the closed product 1303 with a capillary filling technique.

In a second preferred embodiment a sacrificial moulding technique has been used to obtain e.g. a broad band splitter wave guide structure. The microporous product of PES with a dense and smooth skin layer, FIG. 14 shows a SEM picture of a topview of the product, is directly capillary filled with a suitable core layer with a height of 80 micron. The aspect ratio of the small structures of the sacrificial mould at the beginning of the splitter are approximately 80/5. A smooth coverplate with a slightly lower refractive index than the corelayer has been in close contact with the sacrificial mould during capillary filling. Next the sacrificial mould is being dissolved in a NMP solution, a relatively fast process, typical within a few minutes, due to the microporous properties of the product. Finally the core guide structure attached to the cover plate is being covered with a cladding layer with the same refractive index as the cover plate.

Many different materials may be used for the construction of these devices, emphasised is that the (non)solubility of the different materials in different solvents is a prerequisite for the manufacturing of these devices. Materials that may be applied for the mould, the core and cladding layer can be made with acrylate and methacrylate monomers, such as polymethylmethacrylate, polybutylacrylate, polyethylhexylacrylate, polyisodecylacrylate, polyhydroxyethylacrylate, polyhydroxypropylacrylate, polycyclohexylacrylate, polybutane-dioldiacrylate, polydiacrylate, polyneopentylglycoldiacrylate, polydiethyleneglycoldiacrylate, polydiethyleneglycoldimethacrylate, polyhexanedioldiacrylate, fluorinated versions hereof and photopolymerizable versions hereof for in situ patterning. Other useful transparent polymers include polyacetates, polyesters, polystyrene, PVDF, polycarbonates, polyimides, polyethyleneterephthalates (PET) polycyclobutanes, polycyanates and fluorinated versions hereof. Polyester, PET and polybenzocyclobutane are also very suitable as a substrate material.

Optical gratings can also be produced from many materials with different refraction index, with different aspect ratio's and due to the elasticity of the nanoporous transparent layers even negative tapering profiles are obtained (FIG. 13B). A nanoporous optical transparent PVDF sheet 1320 with a thickness of 20 micron with a microstructure 1321 for a 1.3 micron wavelength filter has been obtained with a phase separation process, Next a layer of Ag is deposited with a thickness of 80 nm 1322. Next the grooves are self aligned filled with a photolacquer layer (Shipley resist) 1323, the Ag at the ridges is then dissolved in diluted sulphuric acid and the Ag in the grooves is provided with a thin protective layer. This method can of coarse be used for many different optical applications like fotonic crystals and Compact Disc digital bits with a high aspect ratio, and non-optical applications including the self aligned manufacturing of isolated magnetic domains on a e.g. polyimide tape foil with dotsizes smaller than 100 nm. The dots can be placed on the bottom of a suitable multiwell structure, or preferably on top of pillar shaped structures with a high aspect ratio and a slightly negative tapering profile. The magnetic structures can of coarse be sealed with an abrasion resistant coating.

EXAMPLE 6

Photovoltaic Cells, Transparent Conductive Boards and Electroluminiscent Displays Products according to the invention have been used, as a textured template for enhanced optical properties like scattering and absorption of the light in the photovoltaic (PV) regions, to create surface enlargement of photovoltaic layers with high aspect ratio structures for e.g. amorphous silicon and conducting polymer solar cells and to facilitate capillary filling of the dye fluid in dye sensitised $TiO_2$ solar cells, The invention enables the roll-to-roll manufacture of photovoltaic foils or devices, while at the same time making it possible to use any desired micromoulded structure to improve the function of the PV layers.

According to the invention products have also been used as a temporary product for (high) temperature sputtering of a transparent conductive oxide (TCO) like indium or fluor doped tinoxide and as an electronic circuit board with different wiring thickness dimensions for conductive polymers like polyannile, polypyrrole, polyethylenedioxythiophene (PEDOT) and polyphenylenevinylene (PPV).

Amorphous silicon PV cells are known structures which comprise several layers, usually alternating n-doped, intrinsic, and p-doped silicon, and which essentially have the ability of generating electric current from incident light. To this end, the invention relates to a method which comprises the following subsequent steps:

providing a temporary product obtained with phase separation,
applying a transparent conductor (TCO) layer (photo-electrode),
applying photovoltaic layers,
applying a back-electrode layer
applying a (permanent) carrier
removing the temporary product, and, preferably,
applying a top coat on the side of the transparent conductor layer.

Although the TCO layer will generally be deposited directly onto the temporary product with a thickness not exceeding 100 nm (sometimes preceded by one or more extremely thin layers serving as a process aid), it is also possible after providing the temporary product to first apply an eventual very thin protective (gas tight) layer and/or metallisation electrodes, on the said temporary product, and then the TCO layer, followed by the other layers making up the PV device.

The product according to the invention has been provided with very small micro-structures in the 50-1000 nanometer range. Namely, in order for any PV cell to operate efficiently, it is desired that incident light be scattered through the PV structure as much as possible. To this end, the PV cell's surface, as well as the other layers, needs a certain texture, e.g., such that the surface comprises a plurality of optical prisms (which lead to incident light breaking and spreading through the PV cell). While a normal scattering texture is preferred, more preferred is a texture comprising a plurality of adjacent pyramids, thus having alternating protrusions and indentations, the relative distance between which preferably is in the micron range, and more preferably about 100-250 nanometer. It is further preferred that the protrusions and indentations have a rounded shape (e.g., an angle of basis to hypotenuse of maximally about 40 DEG), in order to prevent possible defects in the amorphous silicon layers which may occur in the case of sharp peaks or sharp valleys. Hence, by adjusting the texture of the temporary product the invention essentially allows the texture of the transparent conductor and the PV layers to be tuned in such a way as to eventually give it optimal surface morphology.

With preference the product is also provided with a number of ridges or trenches to electrically isolate different PV regions and with a number of corresponding perforated regions to facilitate later serial connections of alternating photo and back electrodes to create a solar cell with a high output voltage.

Examples of suitable transparent conductive oxides for the photoelectrode are indium tin oxide, zinc oxide, zinc oxide doped with aluminium, fluor, or boron, cadmium sulphide, cadmium oxide, tin oxide, and, most preferably, Fluor-doped $SnO_2$. The TCO or TCOs can be deposited in a known manner, e.g., using Metal Organic Chemical Vapour Deposition (MOCVD), sputtering, Atmospheric Pressure Chemical Vapour Deposition (APCVD), PECVD, spray pyrolysis, evaporation (physical vapour deposition), electrodeposition, screen printing, sol-gel processing, etc. The temporary (sacrificial) product with the texture is preferentially made with a thermoresistant polymer, like polyimide.

The temporary microstructured product can of coarse also be used for many other applications including non temporary ones.

Solar Cells, Light emitting Diodes, Thin Film Transistors and Sensors with Conjugated Polymeric Layers.

Products obtained with phase separation can be applied in various ways to improve the performance of these devices made with elctrically conducting conjugated polymers. Photovoltaic efficiencies of solar cells are seriously hampered because of the mismatch between the mean absorption length of the photons (typical >100 nm) and the mean recombination length of a photon induced electron-hole pair (typical <20 nm) in the active conjugated polymeric layer. Interpenetrating networks of the electron donor material and the electron acceptor material (with a typical interpenetrating length scale of 20-50 nm) have been proposed to yield higher efficiencies. According to the invention a product with a high aspect ratio and a small repeating distance (<100 nm) is used following subsequent steps for the production of a photovoltaic device:

providing a product 1501 obtained with phase separation having a micro structure with a high aspect ratio (>2) and a small repeating distance (<200 mm),
applying the first electrode 1502
applying the photovoltaic layer(s) of a conjugated polymer 1503
applying the second electrode layer 1504
applying a sealing layer 1505

FIG. 15A. shows a SEM picture of a PET product with a spincoated conjugated layer PEDOT with a thickness of ca 50 nm according to the invention with alternating grooves and ridges with a width of 200 nm and a depth of 600 nm. Products according to the invention may be used directly in the device or as a sacrificial mould for the patterning of the nano/sub-micro-structures with a high aspect ratio according to examples FIGS. 15B, 15C. With the use of a sacrificial microstructured polyimide product obtained with a mould obtained with laser interference lithography, a dense optical transparent microstructured polyethyleneteraphthalate product 1501 is formed with high ratio aspect structures (and rounded at the top to reduce short circuit failure) with an initial groove width of 200 nm and a height of 950 nm. A thin TCO layer (thickness on wall <50 nm) 1502 of room temperature sputtered IndiumTinOxyde w as deposited, followed by spincoating of a PV layer 1503 of PPV at high speed (thickness on wall <50 nm). Next a PEDOT (PEDOT:PSS, Bayer) layer 1504 with low speed spincoating was applied filling up the grooves and covering the ridges with a total thickness of 1 micron, followed by sputtering of a thin gold layer 1507 to ensure a low contact resistance. The total device area was 4×4 cm. Contact electrodes 1506 where further provided at regular intervals of 1 nm. As a sealing layer 1505 a glass substrate was used.

Many variations are of coarse possible for the man skilled in the art. The TCO layer 1502 may be substituted for a e.g. a PEDOT on Au (<10 nm) layer, sputtering techniques of metal layers like e.g. Au, Pt, Ca or Al might be used to obtain relative thick (>50 nm) layers on the ridges and the bottom of the grooves to serve as an optical reflector and as an electric conductor, while the thickness on the walls is less than 10-20 nm (optical transparent). Cylindrical shaped structures in this case are more preferred than parallel groove/ridge structures because of inter connectivity reasons. Filling and etching techniques may be employed for selective removal of the electrode material of the top and/or the bottom. The PPV layer 1503 may be replaced by many other single conjugated active polymers, or double layers with an interpenetrating network, or inorganic active layers as silicon, the second electrode layer 1504 may also serve as a photoelectrode etc.

The product 1501 may also serve as a sacrificial layer, to be removed after all the production steps and also the first electrode (in case of a relatively thick layer) may be deposited in a later step together with a sealing layer after removal of the product. According to the invention the advantage is that the photovoltaic layer will be structured according to the microstructure with a high aspect ratio of at least two. The first electrode will normally be a transparent conductive (TC) layer like in the example of amorphous silicon PV device. In case the second electrode layer is being applied as a TC layer the product 1501 does not have to be removed. The product is then preferentially made at least partially of an electrically conductive material.

Transparent and Non-transparent Conductiv Boards

Conjugated polymers are difficult to use as a transparent conductive (TC) layer in comparison with a TCO like ITO because of their increased surface resistivity (typical larger than 1000 ohm-square at a thickness less than 1 micron).

Most conjugated polymers films with a thickness of 1 micron absorb already nearly 80% of the visible light which make them unsuitable as a TC layer. PEDOT (100 nm) films on a very thin (transparent) Au film (<10 nm) have been proposed as an alternative for ITO on glass products but still suffer from a high surface resistivity. With moulding techniques according to the invention TC layers with a reduced surface resistivity can easily be made:

A product 1601 of polyvinyldifluoride (PVDF) with a dense skinlayer is made with a phase separation process having a number of mesas 1603 with a size of 50×50 micron and a number of corresponding channels 1602 with a width of 20 micron and a depth of 25 micron (FIG. 16A).

A PEDOT aqueous solution together with a standard wetting agent (containing isopropanol) is sprayed and/or spin coated at low speed on the product. Due to the surface tension, the nanoporosity of the skinlayer (cf. FIG. 1) and the evaporation the fluidsurface lowers equally and after drying a conductive PEDOT sheet 1604 is obtained with PEDOT wires in the channel 1602 with a cross section of 20×25 micron and between the wires 1606 on the mesa's 1603 a very thin optically transparent PEDOT film regions with a thickness less than 100 nm is obtained 1605.

Alternatively the conductive layer is applied in two steps. First the channels 1602 are filled by casting a PEDOT solution between the mesas. In a second step a PEDOT aqueous solution is spray and/or spin coated on the product at high speed. After drying a thin (typ. 50-10 nm thick) conductive PEDOT sheet 1604 is obtained on top of the mesas with interconnection of low resistivity wires 1606 between the mesas.

Other combinations of various application methods may as well be used.

The surface resistivity of this film with dual thickness has been measured to be about 40 times smaller (250 ohm square) than a similar film with a uniform thickness of 100 nm (10,000 ohm square). The device may be further processed for use as e.g. a solar cell. a light emitting diode board, a thin film transistor board or a sensor. If necessary the product may be dissolved in a suitable solvent. The body 1601 may also be obtained using a sacrificial moulding technique. Of coarse this method is also suitable for the production of (non transparent) flexible electronic circuit board with different wiring thickness dimensions for conductive polymers such as PPV, polypyrrole, PEDOT, etc. Most of the known conductive polymers are not dissolvable in many known organic solvents.

Dye-sensitised ($TiO_2$) solar cells also benefit from products according to the invention.

A monolayer of suitable dye molecules attached to a $TiO_2$ nanoporous material can be activated by an incident photon. An electron will then easily be transferred to the conduction band of $TiO_2$ and next to a collector electrode (photoelectrode). The corresponding hole will subsequently be transferred via a suitable electrolyte solution to a second collector electrode. The function of the elctrolyte (often containing iodium ions) is to reduce (reset) the oxidized dye molecule. The $TiO_2$ is nanoporous to achieve an enhanced surface area (>100×) for the dye monolayer. A dye (often Ruthenium based) monolayer on a flat surface absorbs less than 1% of the incoming light.

Products according to the invention may be used for these solar cells as a temporary product for the production of a TCO electrode layer or to make a polymeric TC electrode layer as explained above. Moulding may also be used to micro-structure the $TiO_2$ layer (cf. FIG. 12) in combination with a suitable moulding material according to example 4, or to provide micro channels in the solar cell to facilitate capillary (re) filling of the electrolyte solution. A microporous (non) transparent conductive board can also be (reversibly) used to contain part of the electrolyte solution and to electrically separate the TiO2 layer from the conductive board electrode.

Fabrication of Single-C Lour and Multic Lour Electroluminescent Pixels Display

A sacrificial microporous moulded mask product of polyimide containing circular channels of 100 microns in diameter (centre to centre spacing 200 microns) and thickness 50 micron was made according to the invention. The product mask was brought into conformial, sealing contact with an indium tin oxide (ITO) layer patterned on a glass plate. An electroluminescent material, tris (8-hydroxyquinoline)-aluminium (Alq3 50 nm) was deposited by thermal evaporation onto the mask and the glass plate. The mask was removed from the glass plate (peeling or dissolving) and left features of Alq3 on the glass plate patterned as circles. An aluminium cathode then was evaporated on top of the arrangement and an electrical potential was applied between the aluminium cathode and the ITO anode to show electroluminescence.

Multicolour pixels based organic electroluminescent molecules can be also created with one mask product (FIG. 17A) and oblique directional evaporation. The mask product is made from polyimide with high ratio aspect structures and subsequently electroplated to enhance the strength. A mask product 1701 made according to the invention containing rectangular openings 1702 of 60×60 microns with upstanding walls 1703 with a height of 60 micron, separated by 20 microns, was aligned and brought into conformial contact with a suitable transparent conductor board provided with ITO divided in conductor tracks with a width of 40 micron (spacing 30 micron) and a length of 1024 pixels. The conductor board may contain openings or pins to guide the mask product 1701 for aligning 1701. The TCB itself may contain electronic components allowing active switching of the electroluminescent pixels. Three differently oriented wall structures 1703 each corresponding with a different colour are shown. First a mixture of 1,1,4,4-tetraphenyl-1,3-butadiene (TPB), which gives rise to blue electroluminescence 1705 thermally evaporated through the mask under an oblique angle 45° and an azimuth angle 0°. Nile Red dye 1706 was then evaporated through the mask to form the red pixels mask under an obl. angle 45° and an az. angle 90°. Alq3 was then evaporated through the mask under an obl. angle 45° and an az. angle 180°. Next a metallic conductor Mg/Ag was orthogonal evaporated covering all pixels. Next the mask was replaced with two shift of 30 micron orthogonal to the conductor tracks of the TCB and Mg/Ag was deposited forming closed conductor trails. A photoluminescence image of red, green, and blue pixels was obtained after removal of the masks and making electrical connections . Three colour micro printine (Ex. 9) in one step with three non-connected microporous printing parts may also be used, as well as capillary filling techniques in which different colour pixels have a different capillary pressure dependent on the pore size of the colour pixel, to obtain e.g. organic and poly-LED display board.

FIG. 17B shows another layout for a transparent conductive board suitable for deposition of the pixels with an inkjet printer. For this the conductive layer 1710 provided with a thin insulating material 1712 is sealed with the flat side on a transparent product such as glass or a transparent polymeric material 1711. The sacrificial mould for making the transparent conductive board has been dissolved. The conductive layer 1710 of PEDOT together with the insulating material 1712 was made in the structure of the sacrificial mould (not shown). Next with an aligned inkjet printer solutions of three different light emitting dyes coumarin 6 (C6), coumarin 47 (C47) and nile red dissolved into a chloroform solution were deposited in the cavities of the conductive layer. After inkjet printing, the display device was loaded into a vacuum chamber. Typically at least 120 minutes were allowed between loading and metal evaporation through a shadow mask to form conductor tracks with Mg:Ag (10:1), followed by the deposition of Ag as a protective layer.

EXAMPLE 7

Microfluidic Boards

Microfabricated lab-on-chips combine sample handling and analysis steps into a single package. Moulded microfluidic system products may consist of pumps, valves, channels, reservoirs cavities, reaction chambers, mixers, heaters, fluidic interconnects, diffusers, nozzles, microsieves, porous media, and other microfluidic components. Such an approach is commonly known as micro total analysis system (TAS). TAS is an ideal approach for continuous monitoring of chemical concentration in industrial, chemical and biochemical processes. As such, the TAS concept has many potential applications in biotechnology, process control, as well as the environmental and medical sciences. Additionally, product materials are also selected for their inertness to critical components of an analysis or synthesis to be carried out by the device, e.g., proteins, nucleic acids and the like. Devices which include an optical or visual detection element, e.g., for use in fluorescence based or calorimetric assays, will generally be fabricated, at least in part, from a transparent polymeric material to facilitate that detection. Also there is a need for polymer-based products that can be produced efficiently in commercial-scale quantities, e.g., in the form of a roll good, and that can be subsequently selectively tailored to perform a variety of functions including heating, mixing, cell sorting, capillary array electrophoresis, combinatorial chemistry, electro-chromatography and adaptations for the use of kinetic inhibition assays, competition immunoassays, enzyme assays and nucleic acid hybridisation assays.

The microfluidic devices and systems of the present invention are capable of broad application and may generally be used in the performance of chemical and biochemical synthesis, analysis and detection methods. Generally, the devices of the invention can replace conventional laboratory equipment and methods, including measuring and dispensing equipment, as well as more complex analytical equipment. In particular, these devices, with their micron and submicron scales, volumetric fluid control systems, and integretability, may generally be designed to perform a variety of chemical and biochemical operations where these traits are desirable or even required. In addition, these devices may be used in performing a large number of specific assays that are routinely performed at a much larger scale and at a much greater cost, e.g., immunoassays.

The devices may also be used to carry out specific operations in the analysis or synthesis of a sample. For example, the devices may include reaction chambers for performing synthesis, amplification or extension reactions. The devices may similarly include sample analysis elements for the detection of a particular characteristic of the sample, such as a capillary channel for performing electrophoresis on the sample or an optical wave guide structure according to the invention. In such cases, and as described previously, devices for use in such detection methods will generally include a transparent detection window for optical or visual detection.

Moulding of such fluidic board products may be proceeded by applying a mouldable material on a rigid support and bringing a mould in line contact with the mouldable material. The net result is a two-layer structure in which a microfluid processing architecture-bearing layer is integrally bonded to the polymeric product. A second product may be bonded to the moulded article to form a cover layer overlying the microfluid processing architecture. Most of the known products have utilised clamp-shell type devices which have problems with sealing and leakage, particularly when products are being formed from polymers.

A mould with micro fluidic structures has been prototyped in silicon with standard lithographic and anisotropic reactive ion etching techniques. The mould can be used directly for making polymeric replica's with phase separation techniques, or the silicon mould is first transversed into an electroplated mould with good mechanical strength properties, like e.g. nickel from Stork Veco. The latter method has the advantage that the mould of nickel (microstructured nickel foil with thickness 50-200 micron) can be wrapped around a drum for continuous production of polymeric fluidic boards FIG. 18.

With such a drum 1801 (diameter 9.6 cm) having a microstructured nickel foil 1802 with a thickness of 100 micron continuously polymeric moulded micro fluidic products have been made with the VIPS technique. The polymer solution containing a high concentration of polyimide, in a 40/60 NWM/acetone solution has been casted with a mean thickness of 300 micron on the nickel foil 1802 at the highest point of the drum 1801. With preference the casting solution 1808 is already pre-saturated with a small amount of water (<1%) to speed up the vapour induced phase separation proc ss. The rotation velocity (clock-wise) of the drum is set at 1 cm/sec. Around the drum a ring shaped air gap 1803 is being provided with a mean channel height of 1 cm in which air saturated with water vapour is led (anti clock-wise), at an elevated temperature depending on the casting settings between 30 and 90° C., from an inlet 1805 to an outlet 1804 and next to a condenser to collect the solvent and water deposit. The mean interaction time of the casting solution with the air is 60 seconds. The phase separated foil 1803 with micro fluidic structures is subsequently taken up by a collecting roll 1309. With preference the phase separated foil 1808 is first adhered to a support foil 1810 bearing the phase separated foil and in a second stage to a cover foil 1811 covering the fluidic structures before pick up by the collecting roll 1809. Support foil 1810 may contain fluidic structures like in- and output ports and liquid channels to form functional components together with the phase separated foil 1803. Instead of a drum also extended belts with the micro-structured mould may be used for the roll to roll manufacturing of these microfluidic structures or other examples according to the invention. Microporous products may also be used itself as a mould to produce products according to the invention. Non-solvent vapour or liquid may be applied through the pores to induce phase separation of the moulded article. Fluids may also be extracted through the pores e.g. in case of colloids suspended in the fluid to induce solidification.

Thermally induced phase separation (TIPS) has been used to make products of Teflon® PFA (from duPontdeNemours) with a dense skin layer facing the microfluidic structures. Teflon® PFA was dissolved in chlorotrifluoretliylene to a 20 wt % casting solution and brought to a temperature of 300° C. The solution was then casted with the aid of a die (die gap 300 micron) on a mould held at a temperature of 200° C. The chlorotrifluoroetlhylene was extracted from the product during two hours in a Freon TF bath. A heat treatment was given for 30 minutes at 300° C. and microscopic examination showed a dense skin layer at the micro fluidic imprint side of the product. (In a next trial the dense skin layer appeared to be absent by precasting the mould with a very thin layer of chlorotrifluorethylene.)

Other polymeric materials are also suited for TIPS such as isotactic polypropylene and Nylon 12 with respectively diphenylether and polyethyleneglycol as appropriate diluents. temperature LIPS can also be used for continuous production. Matrimid 5218 polyimide (CIBA) is dissolved in NMP and acetone. The polymer solution is cast on a long flexible carrier band having a number of flexible micro-structured nickel foil regions. After casting, blowing air having a temperature of from 15-60° C. and a relative humidity of from 10 to 80% in air-conditioning apparatus is fed from an outlet and directed to the surface of the cast film at a velocity of from 0.2 to 20 cm/sec for a period of from 1 to 15 seconds to remove the acetone and to induce a pre phase separation process by the absorption of water from the humid gas (VIPS). The carrier band with the cast film is then transported and dipped in a coagulating bath containing water which is a non-solvent for the polymer and is compatible with the solvent of the polymer. When dipped in coagulating bath for a period of 20-200 seconds the phase separation process (LIPS) finally shapes a solid micro-structured polymeric film, which is then stripped off from the carrier band having the microstructured nickel regions. The band is then transported back to its starting point. The polymeric film is next introduced into a washing street and drying street and finally wound around a collecting roll.

The thickness of the polymeric film can be adjusted by e.g. changing the polymer concentration, velocity of the carrier band, temperature difference (TIPS) between the initial solvent and the nickel structures, the use of a casting knife etc. In order to give e.g. strength to the polymeric film (in case of thin films) during the process (or depending on the applications) it is also possible to precast the polymer on a solid and flexible support layer e.g. a polyester foil during the described TIPS, VIPS or LIPS processes.

According to the invention phase separation techniques are also employed for sacrificial moulding of microfluidic boards. A mould having microfluidic structures with a height of 55 micron is being filted with a suitable phase seapration technique such that a first microporous polymer (e.g. polylactic acid, a blockcoploymer, PVA) layer is solidified with a height of 50 micron. Next a dense or microporous second polymeric layer (e.g. polyimide) is deposited on the mould and the sandwich structure as released from the mould. The first polymeric layer is then covered by a dense or microporous third polymeric layer (e.g. polyimide) and next the first polymeric layer is (sacrificial) removed, e.g. by thermodegradation and vaporisation of the first polymer or by dissolving and leaching of the first polymer through the microporous second and/or third polymeric layer. The second and third polymer layer now define the microfluidic board.

In case of a microfluidic board having a microporous second and third layer one may fill the pores by various methods to either close the pores to prevent any liquid penetration or to functionalise the porous system according earlier described methods.

A manifold of separate microfluidic boards can be stacked on each other to assemble more complex fluidic devices. Macroscopic perforated foils (e.g. obtained by etching or lithography) may be used in the building of a separate fluidic board and perforations herein serve to interconnect the different microfluidic boards.

The present invention provides multi-layer microfluidic systems, by providing additional product layers, e.g., third, fourth, fifth and more product layers, mated with the typically described first and second layers. Microfabricated elements, e.g., grooves, wells and the like, are manufactured into the surfaces between the various product layers. These microfabricated elements define the various microfluidic aspects or structures of the overall device, e.g., channels, chambers and the like. In preferred aspects, a separate microscale channel network is provided between each of the product layers

EXAMPLE 8

Electrophoretic Board

Capillary electrophoresis typically involves the injection of a macromolecule containing sample, e.g., nucleic acids or proteins, into one end of a thin capillary. A potential is then applied along the length of the capillary to electrophoretically draw the materials contained within the sample through the channel. The macromolecules present in the sample then separate from each other based upon differences in their electrophoretic mobility within the capillary. Such differences in electrophoretic mobility typically result from differences in the charge and/or size of the macromolecules. Other factors can also affect the electrophoretic mobility of a given molecule, such as interactions between the molecules and the capillary walls, interactions with other molecules, conformation of the molecule, and the like.

In brief, when an appropriate fluid is placed in a channel or other fluid conduit having functional groups present at the surface, those groups can ionise. For example, where the surface of the channel includes hydroxyl functional groups at the surface, i.e., as in the case of silica, protons can leave the surface of the channel and enter the fluid. Under such conditions, the surface will possess a net negative charge, whereas the fluid will possess an excess of protons or positive charge particularly localized near the interface between the channel surface and the fluid. By applying an electric field across the length of the channel, cations will flow toward the negative electrode. Movement of the positively charged species in the fluid pulls the solvent with them. The steady state velocity of this fluid movement (electroosmotic flow) in the channel is directly proportional to the zeta potential of the surface that is in contact with the fluid being moved (See e.g. WO. 96/04547). An electric field may also be applied orthogonal to the channel, herewith attracting (binding) or repelling cations or anions to the walls of the channel, to alter significantly the electroosmotic steady state velocity of the fluid along the channel.

Capillary electrophoresis methods have traditionally employed fused silica capillaries for the performance of these electrophoretic separations because of the relatively high zeta potential. In more recent applications, this fused silica capillary has been replaced by an etched channel in a solid planar product, e.g., a glass or silica slide or product. A covering layer or product provides the last wall of the capillary.

The required electric field strength to induce sufficient electrophoretic mobility/separation can increase up to 1 kV/cm putting high demands on the dielectric strength and electric insulating properties of the used materials.

Relatively little effort has been made in using poymeric materials for the construction of a capillary fluidic board with typical capillary diameters of 50-75 micron. According to the invention such capillary fluidic boards can easily be made using a mould and a phase separation process with e.g. a polyimide casting solution.

Although some polymeric materials possess sufficient surface potential to support sufficient electroosmotic mobility of fluids in contact therewith, in the case of many polymeric materials, the surface potential is so low that it does not support sufficient electroosmotic mobility, as defined above. As such, systems that employ these polymeric materials, without modification, are largely commercially impractical for use in microfluidic devices, due to the extremely slow rates attainable for steady state fluid transport.

Surface modification of polymeric products may take on a variety of different forms, including coating those surface with an appropriately charged material, derivatizing molecules present on the surface to yield charged groups on that surface, and/or coupling charged compounds to the surface. The surfaces of the microproduct may be modified or activated, e.g., by oxygen plasma. A thin coating of e.g. polydimethylsiloxane, may also be modified by plasma irradiation, which oxidizes the methyl groups present in the polymer, liberating the carbon atoms and leaving hydroxyl groups in their place. This modification effectively creates a glass-like surface on the polymeric material. In a related aspect, detergents with their charged head groups and hydrophobic tails, function as particularly desirable coating materials. Upon passing such materials through the channels of the system, the hydrophobic tails of the detergent will localize to the hydrophobic surface of the product, thereby presenting the charged head group to the fluid layer, creating a charged surface. Selected charged areas may also be selected and prepared using a photolyzable detergent, which photolyzes to produce a positively or negatively charged group. Irradiation of selected areas on the product surface then fields these charged groups in these areas.

Capillary fluidic boards with a microporous medium can also be made using a mould and a phase separation process to manufacture and release a product with a microporous medium from the mould as an alternative for hot embossing or injection moulding techniques. Of coarse the micro or nano porous medium can additionally to electrophoretic mobilitiy be used to also separate the macromolecules on size. A new application is that surface enlargement of the walls can be achieved with the presence of a very thin but microporous layer on these walls, hence creating the possibility of a strongly enhanced zeta potential, which is also very favourable for materials with an intrinsic low zeta potential. Also the electroosmotic steady state velocity can thus be tuned with relatively low voltages induced by an electric field orthogonal to the channel. According to the invention tangential or circular micro grooves with a high aspect ratio can be provided in the walls for similar purposes. Tube or fibre like capillaries with or without a microstucture along the capillary can also be obtained with 3D spinnerets (see example 11).

A mould 1901 with a long rectangular channel 1902 with a cross section of 50×50 micron has been provided with a casting solution of nylon 4,6 (FIG. 19A). A LIPS phase separation has been performed such that after shrinkage of the casting solution the phase separated material 1903 resides only in the channel 1902 (cf. FIG. 1). The phase separation has been carried out in the liquid-liquid demixing regime avoiding the forming of a dense skin layer on the microporous medium 1903 near the walls of the channel 1902 (cf. SEM pictures 9A,9B). After applying electrode material 1905, a second casting solution containing polyimide 1904 has been provided on the mould 1901 and the microporous medium 1903. After solidification the mould 1901 has been released from the product 1903 and 1904. Electrode material 1905 (now fully covering the microporous medium 1903) and fluidic connections 1906 have next been provided and finally a third casting solution containing polyimide 1907 has been applied to cover and form the product.

Figure 19B:
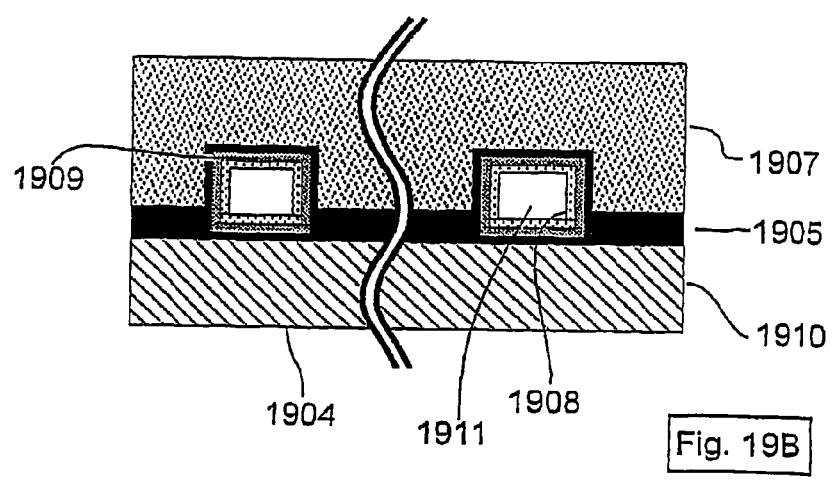

Another embodiment of the invention uses a rim with a cross section of 50*50 micron on the mould (FIG. 19B). On the mould a microporous layer 1908 has been casted with a non-conductive layer on the outside 1909 preferably the skin layer of the casted porous layer 1908. On top of the non-conductive layer a conductive layer has been applied 1905 in the form of a metal like Chromium, Aluminium, Gold or a conductive polymer solution like PEDOT. Next a support layer of polyimide 1907 has been casted on the mould and the conductive layer 1905. After solidification the mould has been released and the channels 1911 with the porous side walls 1908 are sealed on a non-conductive product 1910 like polyimide or glass. Preferably the product 1910 has a conductive layer 1905, an isolator 1909 and porous regions to fully cover the channels 1911.

One may also first form a nanoporous microstructured product functioning as the electrophoretic structure and then coat or laminate with enclosing layers into an electrophoretic or electrochromatography board. In a preferred version of the invention such nanoporous microarchitectures are prepared by colloidal induced phase separation. A nanoporous film with a micro-architecture has been prepared by colloidal induced phase separation. A liquid solution of water (0.4 g), Methylmethacrylate MMA (0.25 g), a redox initiator of ammonium persulphate APS and N,N,N,N-tetrarnethylethylenediamine TMEDA as a crosslinker (0.03 g) and the cationic surfactant (acryloyloxy)undecyltrymethyl-ammonium bromide AUTMAB (0.22 g) forms of a polymeizable bicontinuous microemulsion which is formed prior to casting on the mould. After casting onto the mould the solution was temporarily covered with a glass plate. Light radiation initiated crosslinking and solidification of the oil phase into the microstructured film. Next a second material (polymethylmethacrylate solution) was casted on the film and after solidification the mould was released. With thermoporometry a pore size of about 4-6 nm was determined of the nanoporous film.

EXAMPLE 9

Lithography Micro Printing Tools

Aloys Senefelder used in 1796 a porous stone (in greek, lithos) as a tool for printing by patterning the stone with ink attracting (hydrophobic) and ink repelling (hydrophilic) regions. Lithography for semiconductor mass fabrication and other micro system and nano technology applications has nowadays regained interest on inexpensive micro printing methods as an alternative or complement on current high tech optical wafer stepper technology. A need exists therefore in the art for a convenient inexpensive, and reproducible method of plating or etching a surface according to a predetermined pattern. The method would ideally find use on planar or nonplanar surfaces, and would result in patterns having features in the micron and submicron domain. Additionally. the method would ideally provide for convenient reproduction of existing patterns. Additionally, a need exists for the fabrication of surfaces that can pattern portions (e.g. SAMs) amenable to attachment of biological species, such as antibodies, antigens, proteins. cells, etc., on the (sub)micrometer scale.

The study of self-assembled monolayers (SAMs) is an area of significant scientific research. Such monolayers are typically formed of molecules each having a functional group that selectively attaches to a particular surface, the remainder of each molecule interacting with neighboring molecules in the monolayer to form a relatively ordered array. Such SAMs have been formed on a variety of products including metals, silicon dioxide, gallium arsenide using relief printing with a moulded stamp made from polydimethylsiloxane (PDMS) Whitesides WO9629629). The upper relief part of the stamp provided with a suitable SAM coating is then being contacted with a product with a high affinity for the SAM species and a conformal SAM pattern is formed on the product, e.g. alkanethiol pattern on a goldcoated product. PDMS is a rather elastic and relatively strong material very well suited for reproducible contacting purposes on non planar surfaces, however it lacks a microporous microstructure for enabling functional fluid (ink) transport to the product domains or to enable other functional properties and other deposition techniques as will be disclosed.

Figure 20B:
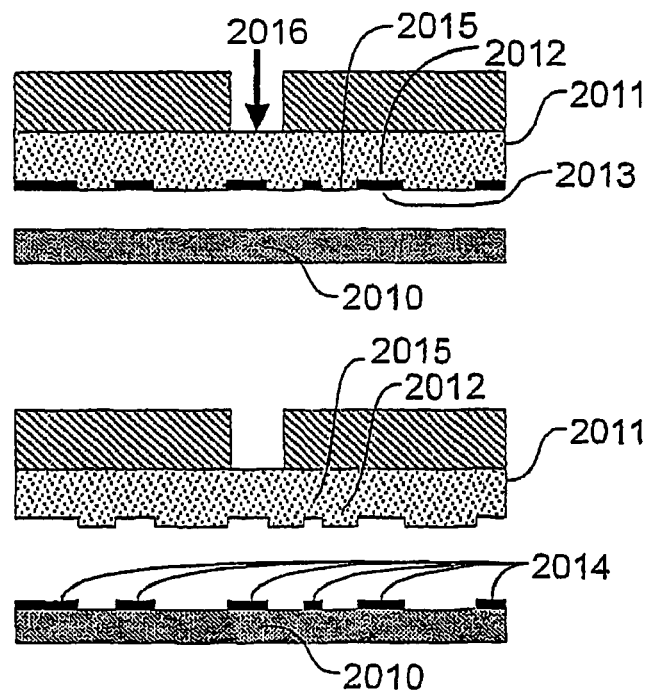
Figure 20C:
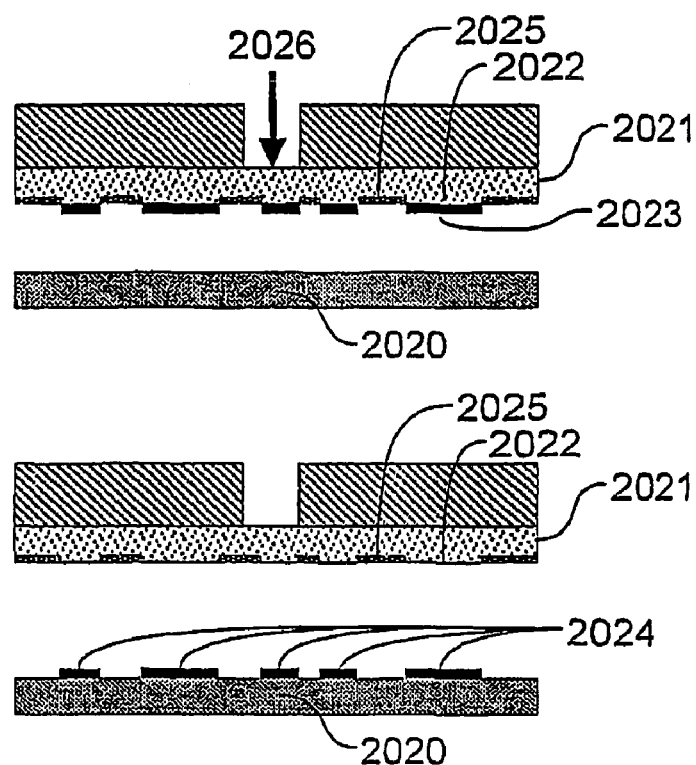

In FIG. 20 three basically different printing techniques are represented.

20A represents the art of relief printing. The upper relief part 2002 of the stamp 2001 provided with a suitable ink coating 2003 is then being contacted with a product 2000 with a high affinity for the ink species and a conformal pattern 2004 is formed on the product 2000. The lower relief part 2005 may be made ink repelling with a suitable coating (e.g. PVA, PVP) in order to avoid smearing of the pattern 2004 of ink originating from sections 2005. According to the invention at least the upper relief part of the stamp 2001 is provided with a macro or nanoporous structure to contain ink or to transport ink from an injection point 2006 for reproduction or continous printing of the pattern 2004 on the product 2000.

20B represents the art of gravure printing The engraved part 2012 of the stamp 2011 provided with a suitable ink coating 2013 is then being contacted with a product 2010 with a high affinity for the ink species and a conformal pattern 2014 is formed on the product 2010. The non engraved part 2015 may be made ink repelling with a suitable coating (e.g. PVA, PVP) in order to avoid smearing of the pattern 2014 of ink from sections 2015. According to the invention at least the engraved part of the stamp 2011 is provided with a macro or nanoporous structure (cf. sem picture 9A,9B, engraved part is microporous, non engraved part has a dense skin layer) to contain ink or to transport ink from an injection point 2016 for reproduction or continous printing of the pattern 2014 on the product 2010.

20C represents the art of planographic printing (i.e. art lithography). The ink delivering part 2022 and the non-ink delivering part 2025 of the stamp 2021 are not determined by a difference in height but are made by the provision of suitable ink-repelling and ink, attracting coatings. The stamp 2022 with a suitable ink coating 2023 on part 2022 is then being contacted with a product 2020 with a high affinity for the ink species and a conformal pattern 2024 is formed on the product 2020. The part 2025 may be made ink repelling with a suitable coating (e.g. PVA, PVP) in order to avoid smearing of the pattern 2024 of ink to sections 2025.

According to the invention part 2022 is provided with a macro or nanoporous structure to contain ink or to transport ink from an injection point 2026 for reproduction or continuous printing of the pattern 2024 on the product 2020. Also in another embodiment part 2025 may be microporous and be filled with an ink repelling medium (e.g. water, Senefelder 1796). Microporous stamps with (alternating) regions with a dense skin layer and adjacent regions with a (porous) layer without the skin layer have easily been made according to the invention by locally removing the skin layer by e.g. oxygen plasma etching with the aid of a perforated mask shielding the remaining dense skin layer regions. Such stamps can also be made by locally perforating the skin layer with a micro needle device according to the invention. According to the invention these stamps are made with a phase separation process with the aid of a mould having patterned regions with sharp protrusions penetrating the microporous layers and patterned regions without such sharp protrusions where a dense skin layer is formed. In case the skin layer is not dense but nanoporous the skin layer can of coarse first be hermetically sealed without sealing the microporous part of the stamp with e.g. a hydrophobic coating (e.g. aliphatic and cyclic olefin-based polymers, or fluoropolymers or silicon based polymers). The stamps may also be sub-patterned through use of photosensitive precursors in the casting solution of the product.

Figure 21A:
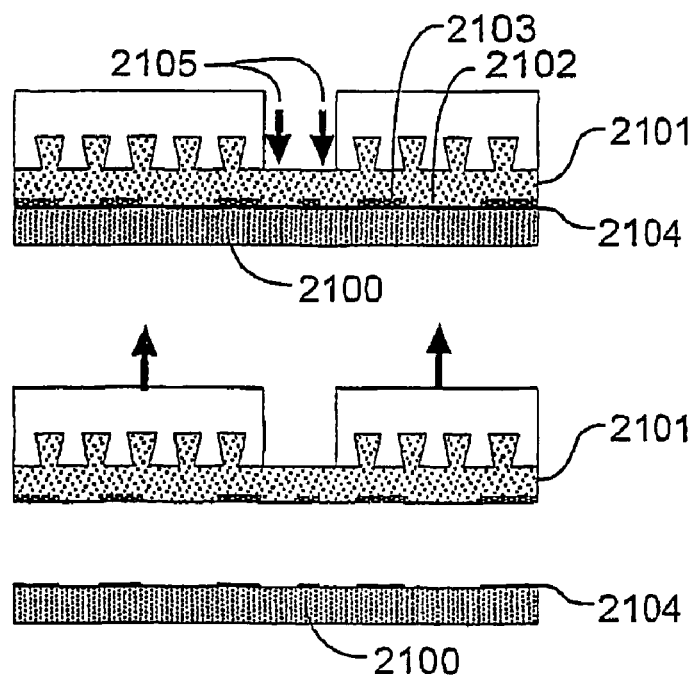

In one embodiment (FIG. 21A) according to the invention a (coplanar) stamp 2101 with alternating nanoporous hydrophilic and dense hydrophobic surface regions (size 100 nm×500 nm) 2102,2103 is locally filled with an aqueous chromium etch solvent 2105 and brought into contact with a product 2100 having a chromium layer 2104 with a thickness of 20 nm. Whereas the dense regions 2103 locally protects the chromium layer, in the nanoporous regions 2102 an exchange between the chromium layer 2104 and the etch solvent results in an locally dissolved and patterned chromium layer 2104. Of coarse many variations ar possible, in order to obtain the patterned layer. Instead of chromium. many other materials or combinations of materials are applicable e.g. aluminium, metal-oxides and nitrides, metals, semiconductors, polymeric lacquer layers, etc. The chromium layer may be replaced by a one phase lacquer layer and the solvent may be replaced by a second phase vulcanising agent for the one phase lacquer layer. Instead of solvents also reactive gases can be used to etch patterns according to the invention, e.g. $SF_6$ to etch and pattern silicon products. FIG. 21B shows a cross-section of a polyimide microporous micro printing tool with a smooth skin layer as obtained with a phase separation process according to the invention.

The microporous stamp according to the invention can also be used to dab or adsorb locally a liquid or viscous layer that has been casted on a product. Dabbing may be improved by locally compressing the microporous regions during the contact of the stamp with the product.

In order to facilitate mask alignment of different mask stamping steps and to reduce thermal expansion differences between the stamps and the product, stamp regions parts (e.g. 2002, 2012, 2022, 2025, 2102,2103) according to the invention are provided on a transparent (e.g. pyrex, borosilicate glass) support material with the same thermal expansion coefficient as the product according to the invention.

With preference a phase separation method has been used to provide the stamp 2001,2011,2021 with the functional microporous parts (e.g. 2002,2012,2022,2025, 2102,2103) using a mould for making the stamp 2001, 2011, 2021 according to the invention. Preferentially the microporous parts leading to the injection point have a high inner porosity to reduce flow resistance and a relatively small total dead volume in order to reduce the amount of adsorbed species.

In some cases it has proven to be useful to first print an ink pattern with the stamp on an intermediate dense or microporous transfer foil, that transfers the ink pattern subsequently to the product, especially foils which have a well defined wetting contact angle with the selected ink medium.

The product 2000, 2010, 2020 may also firstly be provided with a suitable adsorbive nonsplattering or nailoporous (sacrificial) coating 2030 for more adsorption of the ink e.g.

obtained with a phase separation method according to the invention. In another embodiment this nanoporous coating is made by deposition of an aluminium layer with a thickness of 200 nm on a silicon wafer and transforming this aluminium layer to a nanoporous (porosity 60-90%) honeycomb structure with thin vertical walls (pore spacings 10-50 nm) by anodic oxidation techniques well known in the art. Silicon and many other materials with different layer thickness' can be transformed as well with e.g. anisotropic etching techniques for similar purpose according to the invention. After the local deposition of the ink or an e.g. etch resistant lacquer in and/or on this layer, and preferentially dissolving the remaining uncovered layer, the product is ready for further processing steps.

Of course stamps (product) according to the invention may also be used for the formation of micro-structures or micro transfer molding on planar and non planar surfaces of polymeric, ceramic or metallic articles as explained in all described examples (e.g. micro fluidic boards).

EXAMPLE 10

Hollow Fibre and Capillary Polymeric Structures

Figure 22B:
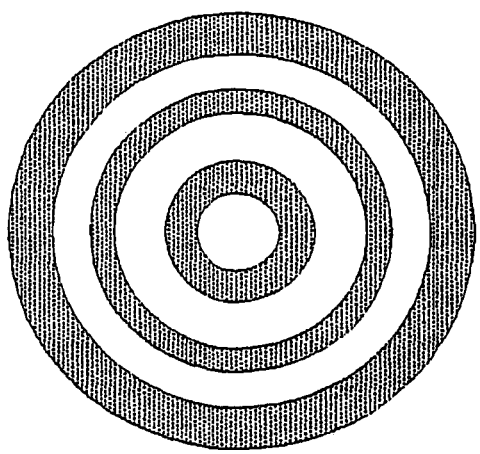

Hollow fibre and capillary polymeric structures are typically found in the field of membrane technology, where they serve as membranes, mostly for separation purposes. Hollow fibre membranes and capillary membrane differ in dimensions, but are both self-supporting cylindrically shaped membranes with typical inside diameters of 10-3000 micrometer. These membranes can either have asymmetric or symmetric structures, which consist of at least one skin layer and a support layer. The skin layer is normally very thin (typically between 0.05-10 micrometer) compared to the support layer (typically between 30 and 500 micrometer) and are present at the shell side, the bor side or both sides of the hollow fibre/capillary membrane. The skin layer is responsible for th separation, while the support only serves as mechanical support with a low as possible flow resistance for the transported species. Hollow fibre/capillary membranes are applied in all kind of separation processes, like gas separation, reverse osmosis, nanofiltration, ultrafiltration, microfiltration, membrane extraction, membrane contactor applications, supported liquid membrane applications, but not limited to these applications. The membranes used today are characterised by either a porous skin or a non-porous, dense skin. The surface of these skin layers are relatively smooth, but might contain some surface roughness, which is caused by the membrane formation process itself (e.g. phase separation) and the polymer used as membrane matrix material in combination with the process conditions, like e.g. the spinning/extrusion rate, the dope composition, the bore liquid composition and/or the flow rate and of the bore liquid. The spinnerets or extrusion nozzles used to produce these hollow fibre/capillary membranes consist of one or more small cylindrical tubes in one or more cylindrical orifices, with smooth tube and orifice walls without specific microstructures. Normally, a rough surface is undesired since in most applications this will enhance membrane fouling. One example in membrane filtration that forms an exception is the so-called low-pressure thin film composite reverse osmosis membrane, which has an extremely rough skin surface, applied on purpose to increase the total surface area and thus enhancing the membrane flux. Since the feed for reverse osmosis is relatively clean membrane fouling due to an increased membrane roughness is negligible. Polymeric hollow fibre/capillary membranes are most of the time produced by a spinning technique in combination with a phase separation process. The initial starting dope solution contains at least one membrane matrix forming polymer and a solvent for that polymer. Often other components like non-solvents, a second or even a third polymer, salts, etc. are added to manipulate the membrane structure. This dope solution is shaped into a hollow fibre or capillary by the use of a spinneret or nozzle and the shape is formed and fixated by a phase separation process. After leaving the spinneret/nozzle the nascent fibre/capillary can either pass through a so-called air gap before the fibre/capillary is immersed in a non-solvent or solvent/non-solvent bath or can enter or being contacted by a non-solvent or non-solvent/solvent bath immediately. The first process is called dry-wet spinning and is normally performed using a tube-in-orifice spinneret/nozzle (FIG. 22A), the latter process is called wet-wet spinning and is normally performed by a triple layer spinneret/nozzle (FIG. 22B). An example of the production of an ultrafiltration membrane by a dry-wet spinning process is as follows:

16 wt % polyethersulfone (Ultrason E 620p, BASF) is dissolved at room temperature in 38.5 wt % N-Methyl pyrrolidone, 38.5 wt. % polyethylene glycol (PEG 200) and 7 wt. water. The polymer solution has a viscosity of 9350 Cp at 25° C. This solution is extruded through a tube-in-orifice spinneret/nozzle (needle OD=0.6 mm , orifice OD=1.2 mm) at a rate of 5 m/min at 22.5° C. After passing through an air gap of 10 mm the nascent fibre enters a coagulation bath filled with water of 20° C. As bore liquid a mixture of 40 wt. % water, 30 wt. % PEG 200 and 30 wt. % NMP was applied. After thorough rinsing with water the fibres are immersed in a 10 wt. % glycerol solution for 24 hours after which the fibres are dried in air. These hollow fibres have an outside diameter of 0.97 mm, an inside diameter of 0.67 mm, a pore size of 15 nm, a pure water flux of 1400 L/m2.hr.bar and a BSA retention of 91%.

Phase separation can be established by changing the polymer solution composition (VIPS,LIPS) and/or by changing the polymer solution temperature (TIPS). This can be accomplished by penetration of a non-solvent vapour into the polymer solution, penetration of a non-solvent liquid into the polymer solution, evaporation of solvent from the polymer solution, diffusion of solvent out of the polymer solution, increasing or decreasing the temperature of the polymer solution.

Figure 24B:
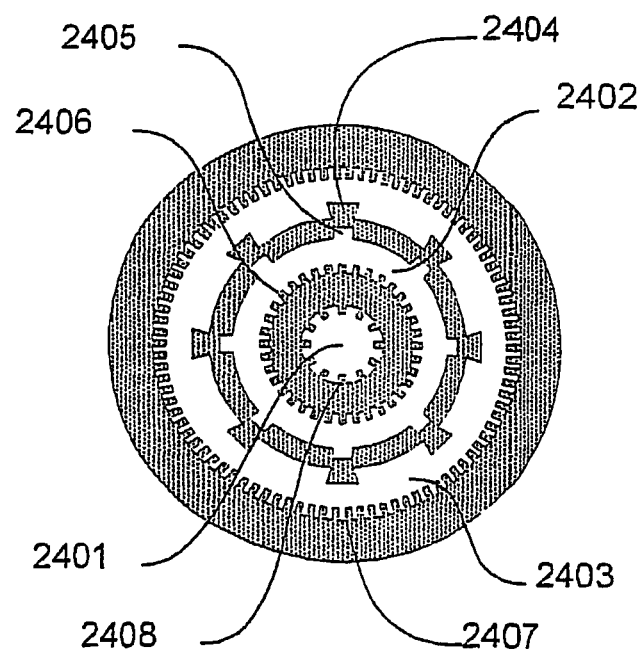

Using moulded extrusion nobles or spinnerets in combination with a phase separation process according to the invention it is now possible to provide any shell or bore surface layer with 3D microstructures (FIGS. 24A, 24B) such as micro grooves and ridges 2413, 2414, 2408, 2407, 2406, 2405, 2404 along the length of the fibre/capillary. Typical dimensions of these micro-structures are between 1 and 200 micron with an aspect ratio up to 10. Other dimensions are also possible demanding on the specific application. According to the invention it has been shown for the first time that such micro-structures with a high aspect ratio can be made and more important that the actual membrane surface can be completely covered by micro-structures with a substantial uniform thickness of the skin layer. A clear advantage of such microstructures is of course a surface enlargement of the membrane layer and hence an improved filtration flow rate, analogue to the low-pressure reverse osmosis membranes. By providing narrow spaced grooves with an aspect ratio of two to five along the tube it is possible to have a membrane surface enlargement up to a factor two to five. If such grooves spiralise along the fibre/capillary also Dean and/or Taylor vortices will be induced of the medium/liquid flowing along the grooves. This will diminish the build-up of a cake layer during filtration and will apart from the surface enlargement contribute additionally to the filtration permeate flow rates. The hollow fibre/capillary membranes according to the invention may also be bent (spiralised) during assembly in a filtration module to induce additional Dean vortices in filtration runs. Grooves may be provided on the membrane's bore surface, but could also be provided on the shell surface in order to diminish the flow resistance of the permeate through the module, while maintaining its supporting properties.

A proof that these micro-grooves can really be provided shows the following example:

25 wt % Polyimide (Matrimid® 5218, Ciba Geigy) is dissolved at 50° C. in 33.75 wt % N-Methyl pyrrolidone, and 22.50 wt % acetone. This solution is extruded through a tube-in-orifice spinneret/nozzle (needle ID=0.2 mm, orifice OD=0.5 mm) at a rate of 8 m/min at 50° C. After passing through a temperature (50° C.) and humidity (<10%) controlled air gap of 200 mm the nascent fibre enters a coagulation bath filled with water of 20° C. As bore liquid a mixture of 30 wt. % water and 70 wt % NMP was applied. After thorough rinsing with water the fibres were immersed in ethanol for 4 hours followed by immersion in hexane for another 4 hours, after which the fibres were dried in air. These hollow fibres have an outside diameter of 0.53 mm, an inside diameter of 0.41 nm, an oxygen permeance of 4.0×10-6 cm3.cm-2.s-1 cm.Hg-1 and an ideal oxygen/nitrogen selectivity of 6.8. The calculated dense skin layer thickness is around 0.4 micrometer. Looking at the shell surface (skin layer) imprinted lines or micro-grooves in the direction of the fibre length have been made. Since the fibre is perfectly gas selective the micro-groove have not damaged the skin layer. This example proofs that microgrooves can be provided to hollow fibre/capillary surfaces.

Another advantage of creating such micro-grooves (FIG. 23, SEM picture cross-section micro structured gasfiltration membrane of polyimide) of a certain shape might be the inter-locking effect the grooves can have when co-extrusion of two polymeric layers is performed. An example of such an inter-lock structure 2404, 2405 is given in FIG. 24B. Applying the triple layer spinneret a first polymeric solution can be extruded through the first orifice 2402, while a second polymeric solution can be extruded through the second orifice 2403. This way a composite hollow fibre structure can be produced. The production of such a composite structure would be desirable e.g. when a polymer is applied, which is responsible for the functional properties and is very expensive. A thin layer of this material is often sufficient to create the desired structure with its functionality (e.g. certain pore size, certain porosity, certain selectivity for gasses, liquids, vapours, etc.) the second layers only acts as a mechanical support layer. When two materials are chosen, which are very different from each other, like an elastomeric material (e.g. PDMS, EPDM) and a glassy material (e.g. PSF, PES, Nylon, PI) or a hydrophobic material (e.g. PSF, PES, PI) and a hydrophilic material (e.g. sulfonated PES, carboxylated PES, sulfonated PEEK, sulfonated PSF) the adhesion between the two layers can be very problematic. Not only will these materials behave differently in the membrane forming process, which can cause delamination, but later, during application these materials might show different swelling or expansion in certain environments (liquids, vapours, temperature, etc.), which can results in delamination of the two layers as well.

An example of the production of such a laminated co-extruded hollow fibre follows:

A first polymer solution consists of 17 wt % polysulfone (Udel P3500, Amoco) dissolved in 52.4 wt % N-Methyl pyrrolidone and 30.6 wt. % diethylene glycol. A second polymer solution consists of 30 wt. % sulfonated polyethersulfone, 35 wt. % N-Methyl pyrrolidone and 35 wt. % acetone. The first solution is extruded through the first orific of a triple layer spinneret 2402 (needle OD=0.6 mm, 1st orifice OD=1.0 nm, 2nd orifice ID=1.1) and the second polymer solution is extruded simultaneously through the second orifice 2403 both at a rate of 6 m/min at 50° C. The second polymer solution was extruded at a rate of 0.43 ml/min. After passing through an air gap of 30 nm th nascent fibre enters a coagulation bath filled with water of 20° C. As bore liquid a mixture of 25 wt. % water and 75 wt. % NMP was applied. After thorough rinsing with water the fibres were immersed in a 10 wt. % glycerol solution for 48 hours, after which the fibres were dried in air. The polyethersulfone layer was porous and had a thickness of approximately 120 micrometer, while the sulfonated polyethersulfone layer was rather dense with a thickness of 2 micrometer.

Beside hollow fibres/capillaries also solid fibres/capillaries can be produced with micro-structures on the shell side of these fibres/capillaries, analogue to the production of hollow fibres/capillaries. The only difference in the production process is that the needle is not present and a bore liquid is not applied or a tube-in-orifice spinneret/nozzle is used and instead of a bore liquid a polymer solution (either the same polymer or a different polymer) is extruded parallel to the polymer solution coming from the first orifice. Applying the triple layer spinneret/nozzle even a third polymer solution (either the same polymer as in the first orifice or a different polymer as the first orifice, but similar the polymer in the bore or even a complete different polymer than applied in bore and first orifice) can be extruded in parallel. A certain micro-structure on the shell of solid fibres/capillaries might be desirable to improve adhesion of certain species like pigments, biological cells, etc.

Creating micro-structures on the bore surface of the fibres/capillaries can be achieved by structuring the needle of the extrusion nozzle or spinneret either at the needle's inside 2408 or outside 2406, 2414 surface. Creating micro-structures at the shell side of the fibres/capillaries can be achieved by structuring the surface of the tube that forms the outside border of the orifice 2413, 2407. Structuring the needle (either inside or outside or both) and the tube forming the outside border of the orifice 2413, 2414, 2407 of a spinneret/nozzle can also be applied to create micro-structures on both bore side and shell side of the fibres/capillaries. To be able to create spiralised structures the needle or orifice containing the texture should be rotating (with or without forward and backwards motion) or the polymer dope should be leaving the nozzle/spinneret in a spiralized flow direction. At a high level of spiralisation nearly orthogonal structures can be made with respect to the length of the capillary. Once the micro-structure is imprinted in the polymer dope solution this structure should be maintained until the structure solidifies by phase separation. This can be achieved by using a highly viscous polymer dope and/or by instantaneous precipitation of the polymer dope after leaving the nozzle/spinneret The above discussed experiments of creating micro-structures in hollow fibre and capillary polymeric surfaces are not restricted to fibres or capillaries with membrane functionality only. Micro-structures can also be applied to e.g. capillaries for capillary electro -kinetic, -phoresis, -chromotography, optical fibres/amplifiers and also biomedical FIG. 6) applications even solid fibres or solid capillaries obtained with and without a phase separation process.

EXAMPLE 11

Flat Sheet and Tubular Polymeric Structures

Analogue to hollow fibre and capillary polymeric structures flat sheet and tubular polymeric structures can be found in membrane technology, where they serve as membrane or barrier, mostly for separation purposes. Flat sheet polymeric structures can also be found in packaging, laminates, etc., but are then produced by a different production process like melt extrusion, blow moulding, vacuum suction, etc. These films are produced from a polymer melt while membranes are normally produced form a polymer solution by a phase separation process. Flat sheet polymeric membranes are prepared as self-supporting sheets or as composite structures where the polymeric film is supported by a woven or non-woven cloth. The woven or non-woven cloth provides additional mechanical support to the membrane. These wovens or non-wovens can be made of polyethylene, polypropylene, polyester, polyphenylsulfide, carbon, etc.

For similar reasons as for hollow fibre/capillary membranes 3 dimensional micro-structures can be introduced in the surface of a polymeric film, on the top side, the bottom side or both sides. Micro-structures on the membrane sheet can also be used (e.g. ridges along the permeate side with a height between 50 en 500 micron) as a spacer between two membrane sheets or as a turbulent promoter in e.g. flat sheet plate and frame modules and spiral wound modules. According to the invention a dense pattern of ridges with a length of approximately 2-6 times the cross flow channel height and placed oblique (preferential 20 to 70 degrees) relative to the mean cross flow direction will enhance the mass transfer coefficient and will counteract the build-up of a cake layer. Ridges contributing to turbulent promotion may differ in e.g. height with respect to the height of the spacer. Such ridges may be provided with an oblique upper plane in order to promote turbulence or to guide fast laminar flow streams towards the membrane layer to inhibit the build up of a cake layer. Ridges may also be provided on the membrane layer orthogonal to the cross flow direction to induce turbulent flow. This can be accomplished by structuring the casting knife or roll, which is in contact with the top side of the film or by structuring the support layer (this could be a plate or roller) on top of which the polymeric film is casted, rolled or sprayed. Again, it is important that the structures introduced in the nascent polymeric film remain their original shape until phase separation solidifies and fixates the ultimate structure. This can be accomplished by using highly viscous solutions and/or defining systems that instantaneous demix after the micro-structure has been introduced. A difference between films and fibres/capillaries is that the nascent polymeric film can be in contact with the support on which the film is provided, while phase separation is induced. This way the microstructure is present at the bottom side of the film, analogue to the methods described in earlier examples.

When a polymeric film is spread on a narrow strip of woven or non-woven support this strip can be winded spirally and welded on the edges contacting each other. This way a tubular membrane or polymeric structure is produced.

EXAMPLE 12

Atomisation Nozzles

Atomisation nozzles for the production of emulsions (water/oil, o/w), double emulsions (w/o/w, o/w/o), foams or nebulae's (spray) for industrial, medical and many other applications, like inkjet printing, spray drying, spray cooling, spray coating, Electro spraying with or without a reinforcing support can easily be made according to the invention. Such nozzles can withstand high pressures by the provision of a thick support. Flow resistance of these nozzles can be reduced in diminishing the length of the nozzle channel or by the provision of tapering nozzle orifices. The local thickness of a perforated membrane or nozzle orifice can be in the order of 1 micron.

FIG. 25 depicts one example of such a nozzle device for deep pulmonary inhale applications. A reinforced sterile prefilter (pore size less than 0.45 micron) 2501, a reinforced nozzle device 2502 with tube shaped nozzles 2503 with a length of 3 micron and an inner radius of 1.6 micron, and a reinforced flow guidance plate 2504, have been made according to the invention with moulds 2505,2506,2507. The plate 2504 has openings of 50 micron (typical between 10-100 micron) and the distance between the nozzle plate 2502 and the flow guidance plate 2504 is 250 micron (typical between 100 and 1000 micron). The flow guidance plate 2504 serves as an aid to promote (e.g. air) coflow 2500 along the liquid jet 2508 coming out of the nozzle 2503. Depending on the exact flow conditions the point of e.g. Rayleigh break-up of the jet in droplets as well as the diameter of the jet and the droplet size can be tuned. Coflow will also generally reduce coalescence of formed droplets. Above the coflow plate a tangential flow can be applied to further avoid coalescence and to carry the droplets to the atomisation device outlet.

EXAMPLE 13

Chip Interconnection Grids

Rapid advances in microelectronic devices are continuously demanding a finer pitch connection between electronic packages and a printed circuit board (about a few hundred micrometer pitch or less). To meet this demand as well as the demand for low cost electronic packages, surface mount technology (SMT) has expanded its shar over the conventional plated-through-hole (PTH) technology for the last twenty years. At present, more than two thirds of integrated circuits (IC) including both memory and logic devices are assembled by SMT. SMT packages commonly found in a PCB are leaded chip carriers such as small outline integrated circuits (SOIC), plastic leaded chip carrier (PLCC), quad flat pack (QFP), thin small outline package (TSOP), or tape carrier package (TCP). These leaded chip carriers, mostly plastic packages, depend on a perimeter connection between an IC package and a PCB. The perimeter connection scheme of SMT packages has reached its limitation in terms of connection pitch and I/O capability.

To relieve the limitations of perimeter connections and thereby to increase the packaging density, area array connection schemes have recently become popular. Some of the area array packages developed for SMT include ball grid array (BGA) package, solder column grid array (SCGA), direct chip attach (DCA) to PCB by flip chip connection (FCBGA), tape ball grid array (TBGA), or chip scale packages (CSP). Among them, BGA is the most popular one, where solder balls connect a module carrying an IC to a PCB. This technology is an extension of the controlled collapse chip connection (C4) scheme originally developed for solder bump connection of multiple chips to a ceramic product.

There are several options depending on the choice of module materials, such as plastic BGA, ceramic BGA, and tape BGA. Ceramic BGA is more costly than plastic BGA, but it has a better proven reliability over the plastic BGA. However, one major weakness of ceramic BGA is a large mismatch of thermal coefficient of expansion (TCE) between a ceramic module and a polymeric PCB. This limits the maximum size of ceramic BGA module to be mounted on a PCB, which is about 32 mm@2 with state-of-art technology. For a ball pitch of 50 mil, this BGA module can have about 625 I/O connections. Plastic BGA is better in terms of TCE mismatch because of a better materials compatibility between the module and the PCB product materials. Polyimide (e.g. KAPTON®) or polyetherimide (ULTEM®) is often used as the plastic material, it is strong heat resistant and has a relatively low dielectric constant (2-2.5) in comparison with ceramic materials (2-4).

More particularly, an aspect of the present invention is an improved production method of ball or stud grid array packages between chips and a ceramic or organic Printed Circuit Boards (PCB) by application of products obtained with a phase separation process. Microporous and virtually dense e.g. polyimides obtained with phase separation techniques have an improved dielectric constant (e.g. <1.8), have favourable deformable semi-elastic properties to buffer the thermal mismatches between the chip (package) and the PCB, and can easily be provided with bumps, wiring channels and vias with use of a mould according to the invention. Microporous products can subsequently be filled with functional materials as e.g. (conjugated) mono- or poly-mers, functional agents, inorganic materials etc. to improve e.g. the strength, the thermal conductivity, the elasticity, the coefficient of thermal expansion, the dielectric constant, the dielectric strength and/or the magnetic susceptibility of the product The filling of the micro pores can be done simultaneously with the well known underfill step (filling space between chip and grid array with e.g. an epoxy) during assembly. The casting liquid may also contain functional materials like (e.g. BeO, SiC particles to improve thermal conductivity of the product) before phase separation is performed on the mould according to the invention. Of coarse products according to the invention can also be used for sacrificial moulding of any other functional grid array of a polymeric, metallic or inorganic material. The product may be provided with well defined vias and to provide one or more stepped bumps to secure and guarantee reproducible layer thickness for the solder or connection material to the chip. Multiple layered grid arrays can be assembled with functional metallic or conjugated polymeric shielding regions for the ground and power supply leads, herewith decreasing the inductance and crosstalk between different high speed (>400 MB) leads. Channels may be provided in the grid array for optical wave guide layers (fibres) for transmittance of optical signals between the chip and the PCB (cf. example 5: waveguides). The product may also be formed with heat slugs to facilitate heat dissipation.

A polyimide solution (25 wt % Matrimid 5218 in NMP) has been casted on a mould and after a LIPS phase separation with ethanol as a non-solvent bath a polyimide moulded grid array 2601 with a thickness of 200 micron and a body size of 40×40 mm with 2303 ball via's 2602 with a ball pitch of 800 micron and a dielectric constant of 1.85 has been obtained (FIG. 26) with a very thick and dense skin layer. On one side of the grid 2601 a number of grooves 2603 are provided with a cross section of 50×80 micron and extending from the ball via's 2602 to the centre of the grid array 2601 to via's 2604 with e.g. a larger upper diameter than the ball via's 2602.

According to the invention the grid 2601 is contacted to a conducting base plate 2605 and with a (stirred) copper electroplating bath the via's 2602, 2604 and the grooves 2603 have been provided with copper 2606. Because of the smaller diameter of the ball via's 2602 the growth of copper herein is slower (more diffusion limited by the smaller opening 2602) than in the via's 2604 after the grooves have been filled with copper. The plating process is preferentially stopped after a small overgrowth 2607 of the copper at the via's 2604, but before the via's 2602 have been filled with copper. The copper leads are therefore also mechanically anchored in the product and the via's 2602 may further be filled with an electrically insulating material. Similar via's 2602 with or without tapering walls may be present in the product to improve anchoring and/or facilitate electroplating of (long) leads. After release (e.g. stripping or etching) of the base plate 2605 the cleaned and dried product is flip chip electrically contacted to a chip 2701 with size 9×9 mm (FIG. 27) with known techniques. Hybrid products provided with conducting leads (metallic or conducting pastes) can be manufactured in many ways according to the invention. Products 2702 and product 2703 with a cavity for the chip 2701 have been manufactured according to the invention, 2704 resembles a heat sink plate. Using more products like 2702 and 2703 make complicated connection schemes for connecting multichip modules or chips with sensors and/or actuators possible. The invention applies also to conventional wire bonded chips and the implementation of conventional lead frames in combination with different products with or without metallisation provisions of the products. Instead of chips the present invention is also applicable to a variety of different semiconductor micromechanical devices, for instance actuators, motors, sensors, spatial light modulators, and deformable mirror devices.

EXAMPLE 14

3D Electroplating with a 3D Moulded Mask Product

Moulded mask products according to the invention have been used to electroplate 3D metallic structures. In a first example a flat product of polyimide with a thickness of 100 micron and having further a lead frame structure for an electronic chip is dipcoated in an electrically conductive conductive polymer Baytron® P from Bayer chemicals. Next an electroless nickel layer with a thickness of 2 micron was deposited on the product. The lead frame product was then placed in a silver electroplating solution (Technic Silver E2, Technic, current density ~10 mA/cm2) until a 10 micron thick silver layer was obtained. Many other phase separated articles according to the invention like encoder disks, microsieves, nozzles, shadow masks etc. can be provided with an metallic or conductive coating. In this way all presently known electroplated articles e.g. encoder disks, microsieves, atomisation nozzles and new articles can be manufactured. In a second example a polyimide moulded 3D structure for a lead frame according to the invention containing circular perforations of 50 micron diameter and a height of 200 micron and interconnected to non perforated grooves with a depth of 50 micron and width 60 micron was brought into conformal, sealing contact with an electrical conducting base plate of copper and put in a nickel electroplating bath. After wetting and during stirring of the bath a nickel layer was deposited in the perforations with a height of 100 micron and also in the grooves. After selective copper etching of the base plate a ball grid array structure of nickel leads with a height of 50 micron and nickel circular mesa's with a height of 200 micron has been obtained. The mesa's can further be provided with a gold coating and solder balls for subsequent connection with a Printed Circuit Board and/or a chip. The polyimide is sufficiently heat resistant for solder connections up to 300 C. The microporous polyimide product showed excellent dielectric properties (dielectric constant 1.8). The polyimide solution for obtaining the product can also be provided with nanosized ceramic particles with a low dilectric constant and a high thermal conductivity like. Depending on the application the polyimide product can also be redissolved to obtain pure metallic or electrically conductive articles. Microporous products can also be transformed to a microporous replica by filling the pores with a suitable material and redissolving the original microporous product. Shadow masks and other structured products that have strict demands on stiffness and thermal expansion are favourable be provided with an appropriate metal.

Electroplated and non-electroplated microneedles (hollow microtubes) have been made with a mould with conical shaped pinholes (outer diameter 100 micron, length 1500 micron). At the centre of the pinhole (outer radius at the bottom 20 micron a pillar with a diameter having a radius of 8 micron and a height of 40 micron is present on the mould. A polyimide phase LIPS separation process as described earlier has been performed leading to a microporous inner body and a smooth conical shaped and very thick skin layer by using ethanol as a non-solvent bath. The polyimide product with a thickness of 2 nm is taken from the mould and dried. After insertion of water on the unpatterned side water droplets were formed at the tip of the needles. Electroplating methods with nickel and gold on the outside of the needles have been performed for reinforcing the strength of the needles. Many therapeutic and non-therapeutic applications are possible with electroplated and non electroplated microporous hollow needle devices of many different materials including biodegradable and non-biodegradable materials.

The invention is not limited to the given examples. Many other applications are equally possible and may be developed by those who are skilled in their expertise. Dissimilar sheets of material that otherwise would not bond well to one another (such as a polymer and a metal) can be more strongly bonded with microstructures extending from one of the sheets and embedded into the other sheet. Such products make valuable laminate composites.

As another example, introducing microstructures to a sheet of material can dramatically change the surface properties of the sheet, such as its surface energy, radiation absorptivity and emissivity, ability to absorb mechanical and acoustic energy, catalytic activity, etc. For example, the rate of heat transfer between an object and the surrounding medium can be dramatically changed by covering the surface of the object with high aspect ratio microstructures, without significantly changing the object's size or weight.

Products according to the invention may be reinforced with supporting structures e.g. non-wovens, they may be provided with many coatings e.g. Pluronics® for wetting and anti-fouling purposes. The terms hydrophilic and hydrophobic can be understood in many other ways, like a polar and polar, or affinity and non-affinity for a given medium not being water.

Patterning tools may comprise e-beam, single and multiple laser interference for e.g. micro printing and solar cell applications. Microporous or micro perforated products may be provided with a hydrophobic coating for e.g. moisture permeating textile.

The non-solvent may also be virtually or totally absent in the vapour and/or the polymer solution during production with a vapour induced phase separation (inversion) process, phase separation is then kinetically inhibited. Phase separation may be initiated if in a later stage the product is brought into contact with an atmosphere containing non-solvent molecules.

The moulds may be provided with additional means, such as coatings or pores for pressurised release or a suction device to facilitate removal of the product from the mould. The moulds may be provided with structures at the border of a periodic structure having a slightly other geometry than in the inner part for compensation of shrinkage differences in the periodic structure in the product.

All claims should be read in relation to the above giving examples. According to the invention products may be used directly to create functional products according to the given examples. The products may also be used as a sacrificial mould to create fictional products of any type of material e.g. polymeric, metallic or ceramic. Microporous sacrificial moulds have the advantage that they are relatively easily dissolved in a suitable solvent or pyrolised than more dense moulds. Microporous open as well as closed moulds can also be used to feed a non-solvent through the pores or to extract a solvent through the pores to induce phase separation and to obtain moulded products according to the invention. A microsieve product may also be used as an open moulding tool to extrude a casting solution through the pores in a non-solvent medium.

The invention claimed is:

1. A method of making a product with a predetermined micro to nano sized structure, comprising:
   providing a mould having a corresponding predetermined micro to nano sized structure at a mould surface;
   contacting a casting fluid containing a casting material with said mould surface;
   subjecting said casting fluid to a non-solvent based phase separation treatment to induce phase separation therein;
   inducing solidification and shrinkage of said casting material by contacting said casting fluid with a non-solvent fluid so as to form a product on the mould surface; and
   releasing the resulting product, which is at least partly solidified, from the mould surface with said predetermined micro to nano sized structure after said casting material has at least partly solidified and shrunken.

2. The method according to claim 1, wherein the mould surface with said predetermined micro to nano sized structure is an exposed surface of said mould.

3. The method according to claim 1, wherein said product is released from the mould for further processing, including further phase separation.

4. The method according to claim 1, wherein the mould is brought in contact with said casting fluid in a continuous process.

5. The method according to claim 1, wherein said non-solvent based phase separation process is selected from the group consisting of a vapor and/or liquid induced phase separation process, a colloidal induced phase separation process, a pressure induced phase separation process, and a reaction induced phase separation.

6. The method according to claim 1, wherein the non-solvent fluid is contained in an immersion liquid during the phase separation process at a concentration larger than 5%.

7. The method according to claim 1, wherein the nonsolvent fluid is contained in a vapor during the phase separation process at a concentration less than 25%.

8. The method according to claim 1, wherein the nonsolvent fluid is dissolved in said casting fluid with a concentration less than 2%.

9. The method according to claim 8, wherein,
said casting fluid comprises a lowest boiling solvent and a highest boiling solvent,
said lowest boiling solvent and said highest boiling solvent have a difference in their respective boiling points of at least approximately 50° C.,
a predominant amount of said lowest boiling solvent is removed and the nonsolvent fluid is miscible with said two solvents, to induce phase separation and solidification of said casting material.

10. The method according to claim 4, wherein said continuous process is a process of continuous sheet imprinting or extrusion with a spinneret having said predetermined micro to nano sized structure.

* * * * *